US011987576B2

(12) United States Patent
Ridky et al.

(10) Patent No.: US 11,987,576 B2
(45) Date of Patent: May 21, 2024

(54) COMPOSITIONS AND METHODS FOR DECREASING, OR PREVENTING OR REVERSING GAIN OF, SKIN PIGMENTATION IN A MAMMALIAN SUBJECT

(71) Applicant: THE TRUSTEES OF THE UNIVERSITY OF PENNSYLVANIA, Philadelphia, PA (US)

(72) Inventors: Todd Ridky, Bryn Mawr, PA (US); Christopher Natale, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 17/480,948

(22) Filed: Sep. 21, 2021

(65) Prior Publication Data
US 2022/0017497 A1    Jan. 20, 2022

Related U.S. Application Data

(63) Continuation of application No. 15/562,725, filed as application No. PCT/US2016/026213 on Apr. 6, 2016, now Pat. No. 11,236,074.

(60) Provisional application No. 62/216,792, filed on Sep. 10, 2015, provisional application No. 62/143,597, filed on Apr. 6, 2015.

(51) Int. Cl.
| | |
|---|---|
| *A61K 8/63* | (2006.01) |
| *A61G 17/04* | (2006.01) |
| *A61K 8/49* | (2006.01) |
| *A61P 17/00* | (2006.01) |
| *A61P 17/06* | (2006.01) |
| *A61P 17/14* | (2006.01) |
| *A61P 17/16* | (2006.01) |
| *A61P 17/18* | (2006.01) |
| *A61Q 19/02* | (2006.01) |
| *C07D 221/16* | (2006.01) |
| *C07D 405/04* | (2006.01) |
| *C07D 491/048* | (2006.01) |

(52) U.S. Cl.
CPC .......... *C07D 405/04* (2013.01); *A61G 17/04* (2013.01); *A61K 8/49* (2013.01); *A61P 17/00* (2018.01); *A61P 17/06* (2018.01); *A61P 17/14* (2018.01); *A61P 17/16* (2018.01); *A61P 17/18* (2018.01); *A61Q 19/02* (2013.01); *C07D 221/16* (2013.01); *C07D 491/048* (2013.01)

(58) Field of Classification Search
CPC .............. C07D 405/04; C07D 221/16; C07D 491/048; A61K 8/49; A61K 31/36; A61K 31/473; A61P 17/00; A61P 17/06; A61P 17/14; A61P 17/16; A61P 17/18; A61Q 17/04; A61Q 19/02
See application file for complete search history.

(56) References Cited

U.S. PATENT DOCUMENTS

| | | | |
|---|---|---|---|
| 3,275,622 | A | 9/1966 | Albert |
| 5,227,459 | A | 7/1993 | Pawelek et al. |
| 2008/0167334 | A1 | 7/2008 | Prossnitz et al. |
| 2009/0197939 | A1 | 8/2009 | Walke et al. |
| 2009/0246156 | A1 | 10/2009 | Kunin |
| 2010/0183528 | A1 | 7/2010 | Maloney et al. |
| 2012/0053245 | A1 | 3/2012 | Baroni et al. |
| 2012/0219514 | A1 | 8/2012 | Bonnichsen et al. |
| 2013/0149341 | A1 | 6/2013 | Miller et al. |

FOREIGN PATENT DOCUMENTS

| | | |
|---|---|---|
| CN | 104083368 A | 10/2014 |
| GB | 1051693 A | 4/1967 |
| WO | 2004072046 A2 | 8/2004 |
| WO | 2007019180 A2 | 2/2007 |
| WO | 2008121850 A2 | 10/2008 |
| WO | 2012122101 A1 | 9/2012 |

OTHER PUBLICATIONS

Extended European Search Report for European Patent Application No. 16777200.3 dated Nov. 16, 2018.
Arnatt, et al., G Protein-Coupled Estrogen Receptor (GPER) Agonist Dual Binding Mode Analyses toward Understanding of its Activation Mechanism: A Comparative Homology Modeling Approach, Mol Inform. 32(7) ,Jun. 2013 ,647-658.

(Continued)

*Primary Examiner* — Jessica Worsham
(74) *Attorney, Agent, or Firm* — Saul Ewing LLP; Domingos J. Silva

(57) ABSTRACT

The present invention includes compounds, compositions comprising the same, and methods using the compounds and/or compositions therein, for modulating skin pigmentation in a mammalian subject. In certain embodiments, the compounds of the invention treat or prevent skin disorders or diseases associated with hyperpigmentation in the subject. In other embodiments, the compounds of the invention act as antagonist to the non-canonical sex steroid hormone receptor GPRE1 and do not bind to a canonical nuclear estrogen receptor (ER). In yet other embodiments, the compounds of the invention comprise acts as agonists to the non-canonical sex steroid hormone receptor PAQR7 and do not bind to a canonical nuclear progesterone receptor (PR).

8 Claims, 18 Drawing Sheets
Specification includes a Sequence Listing.

(56) References Cited

OTHER PUBLICATIONS

Burai, et al., Highly efficient synthesis and characterization of the GPR30-selective agonist G-1 and related tetrahydroquinoline analogs, Org Biomol Chem. 8(9) ,March ,2252-2259.
Burai, et al., Synthesis and characterization of tricarbonyl-Re/Tc(I) chelate probes targeting the G protein-coupled estrogen receptor GPER/GPR30, PLoS One. 7(10)1-10 ,Oct. 2012 ,1-10.
Caboni, et al., Molecular topology applied to the discovery of 1-benzyl-2-(3-fluorophenyl)-4-hydroxy-3-(3-phenylpropanoyl)-2H-pyrrole-5-one as a non-ligand-binding-pocket antiandrogen, J Chem Inf Model. 54(1) ,Sep. 2014 ,2953-2966.
Dennis, et al., Identification of a GPER/GPR30 antagonist with improved estrogen receptor counterselectivity, J Steroid Biochem Mol Biol. 127(3-5) ,Jul. 2011 ,358-366.
Lack, et al., Targeting the binding function 3 (BF3) site of the human androgen receptor through virtual screening, J. Med. Chem. 54(24) ,Dec. 2011 ,8563-8573.
Pang, et al., Progesterone increases nitric oxide synthesis in human vascular endothelial cells through activation of membrane progesterone receptor-α, Am J Physiol Endocrinol Metab. 308(10) ,Mar. 2015 ,E899-E911.
Ramesh, et al., Synthesis and characterization of iodinated tetrahydroquinolines targeting the G protein-coupled estrogen receptor GPR30, J. Med. Chem 53(3) ,Dec. 2010 ,1004-1014.
International Search Report and Written Opinion for PCT International Application No. PCT/US2016/026213 dated Oct. 17, 2016.
PubChem, Substance Record for SID 48409626, create date: Feb. 22, 2008. [retrieved on Jul. 22, 2016]. Retrieved from the internet <htps://pubchem.ncbi.nlm.nih.gov/substance/48409626#section=Top>.
Jian-Bing , "The role of estrogen in the pathogenesis of melasma and the treatment of melasma", Doctoral Dissertations-Medical Health Science and Technology Series, No. 5,, May 5, 2012, Abstract only.
Kelder , et al., "Comparison Between Steroid Binding to Membrane Progesterone Receptor Alpha (mPRalpha) and to Nuclear Progesterone Receptor: Correlation With Physicochemical Properties Assessed by Comparative Molecular Field Analysis and Identification of mPRalpha-specific", Steroids 75(4-5), Apr. 2010, 314-322.
Wiedemann , et al., "Inhibitory Effects of Progestogens on the Estrogen Stimulation of Melanocytes in Vitro", Contraception 80(3), Sep. 2009, 292-298.
Hill, Jeremy P., et al., "An approach to hypopigmentation", The BMJ, Published Jan. 5, 2017, pp. 1-6, Retrieved from the internet <doi:10.1136/bmj.i6534>.
Emedicine health https://web.archive.org/web/20130126074829/https://www.emedicinehealth.com/birth_control_medications_contraceptives/topic-guide.htm, no pagination, 2013.
Kitawaki et al. (J. Steroid Biochem Mol. Bio, 2002, 83(1-5), 149-155).
NIH (https://www.nichd.nih.gov/newsroom/releases/endometriosis), no pagination, 2002.
Sinaii et al. (Human Reprod., 2002, 17(100), 2715-2724).
Kvaskoff, M. et al., Int. J. or Epdemiology, 2009, 38, 1143-1153.
Schmidt, J.B. et al., "Treatment of skin ageing symptoms in perimenopausal females with estrogen compounds", A pilot study. Maturitas, vol. 20, Issue 1, pp. 25-30. (Year: 1994).
Dennis et al., In Vivo Effects of a GPR30 Antagonist. Nat Chem. Biol. Jun. 2009, 5(6), pp. 421-427.
Verdier-Sevrain et al. Biology of estrogens in skin: implications for skin aging. Experimental Dermatology, 2006, 15, pp. 83-94.

FIG. 3A
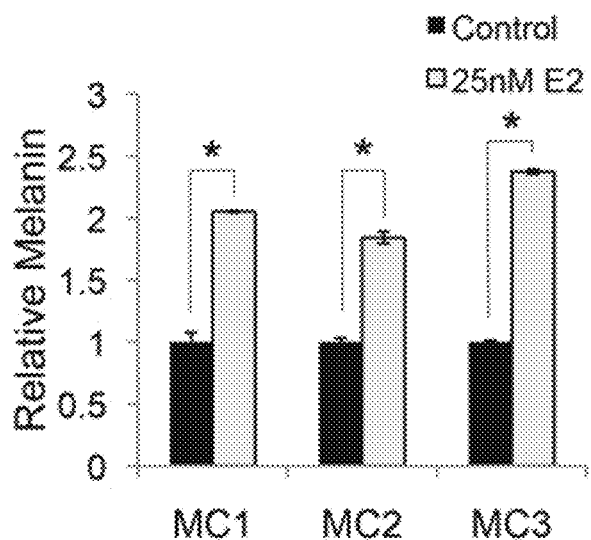
FIG. 3B　　　　FIG. 3C
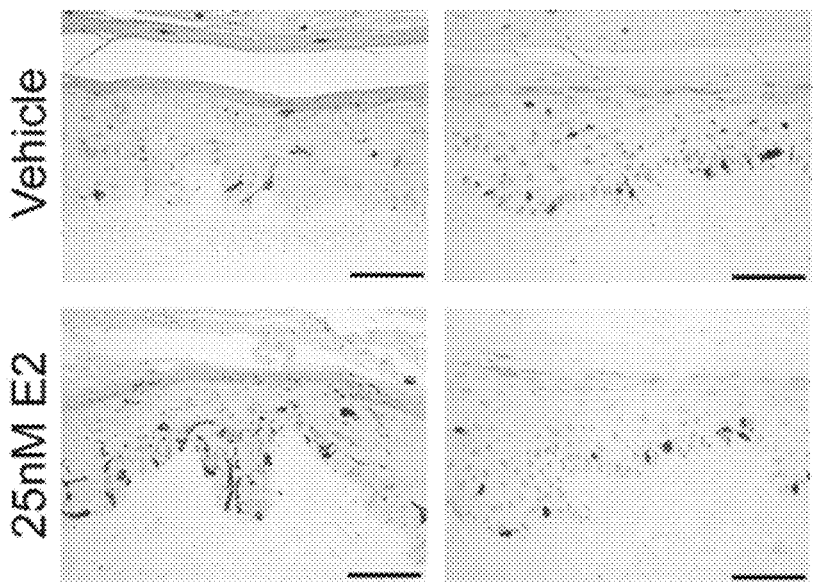
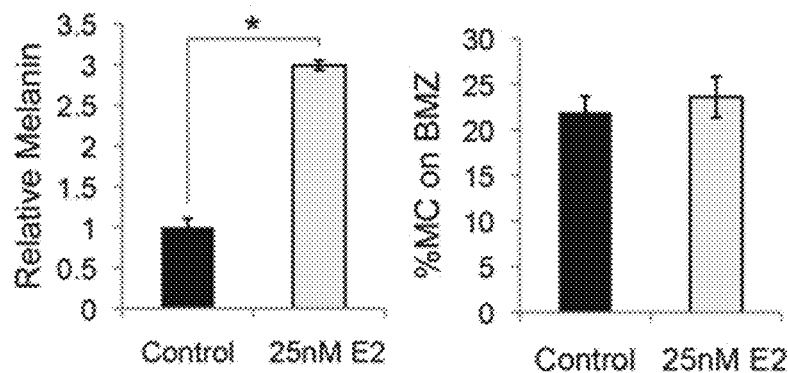

FIG. 3D
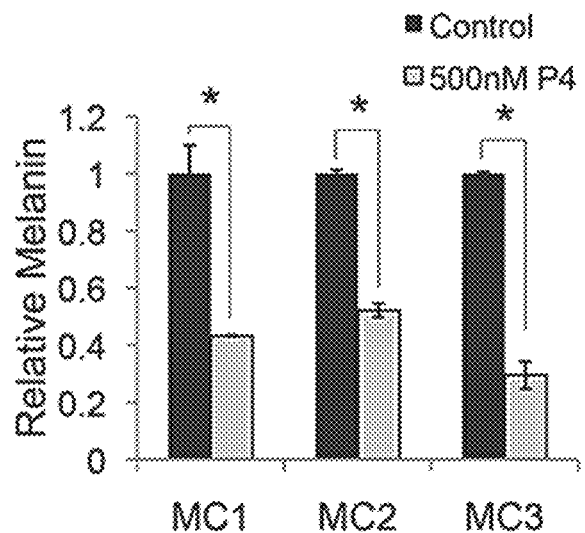
FIG. 3E
Melanin
FIG. 3F
MITF
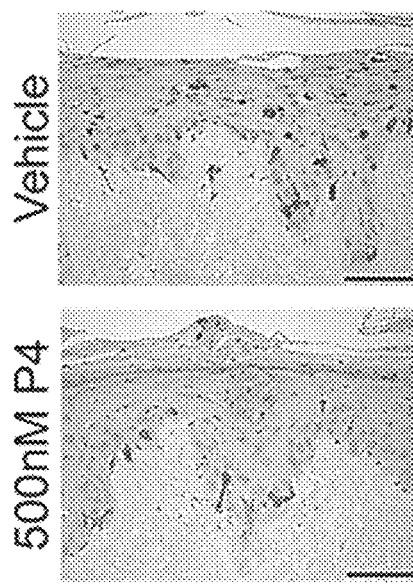
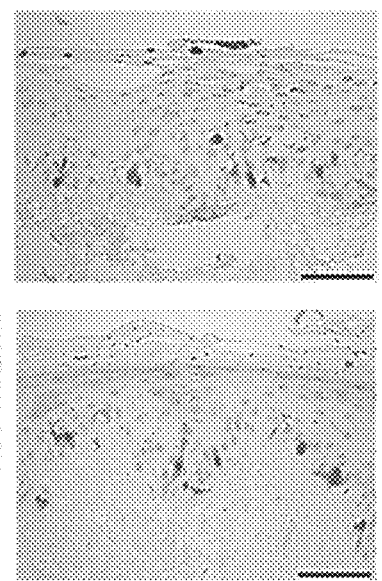
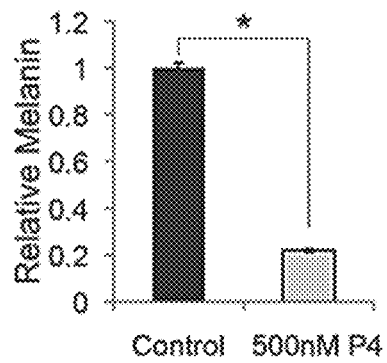
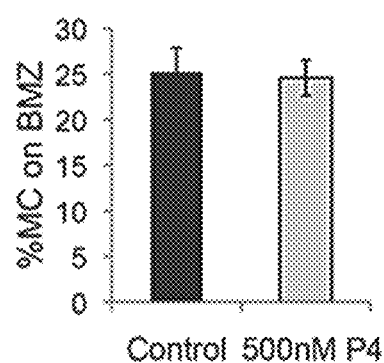

FIG. 5A
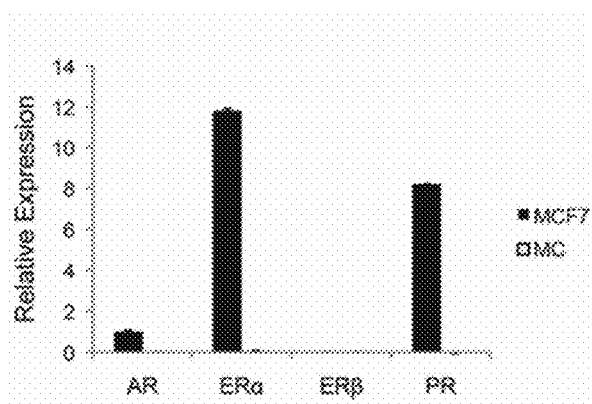
FIG. 5B
| Target | Average RPKM |
|--------|--------------|
| AR | 0.040669553 |
| ERα | 0.266334213 |
| ERβ | 0.852619848 |
| PR | 0 |
| GPER | 2.884739983 |
| PAQR7 | 4.9125 |
FIG. 5C
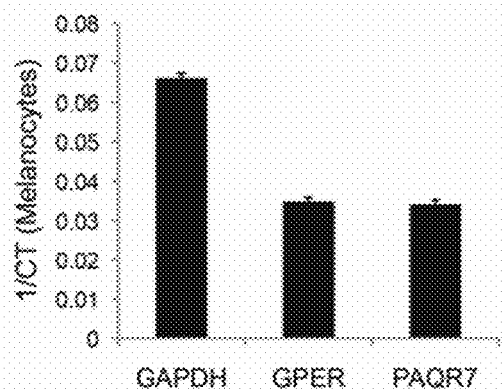
FIG. 5D
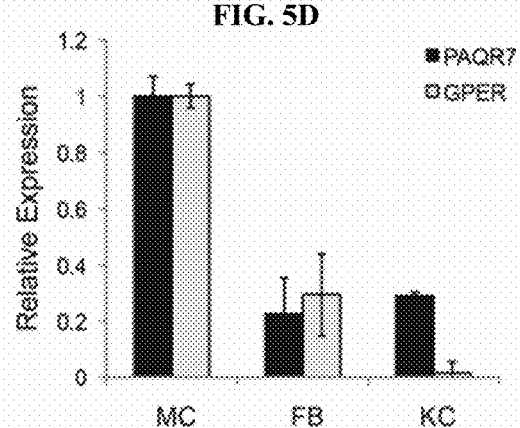

SEQUENCE LISTING

```
<160> NUMBER OF SEQ ID NOS: 23

<210> SEQ ID NO 1
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 1
catgtacgtt gctatccagg c                                    21

<210> SEQ ID NO 2
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 2
ctccttaatg tcacgcacga t                                    21

<210> SEQ ID NO 3
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 3
aaaggtggga tacgaaaaga cc                                   22

<210> SEQ ID NO 4
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 4
agcatccaac aaggcactga                                      20

<210> SEQ ID NO 5
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 5
ggctgcgaga ataactgcc                                       20
```

<210> SEQ ID NO 6
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 6
aatgcggaca cgtgcttttc                                           20

<210> SEQ ID NO 7
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 7
aggtctaccc gccctatctc                                           20

<210> SEQ ID NO 8
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 8
agtagttgtg ctgcccttcc                                           20

<210> SEQ ID NO 9
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 9
gtgctgtaca ggagccgaag                                           20

<210> SEQ ID NO 10
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 10
gtcagtccta ccaggcactt                                           20

<210> SEQ ID NO 11
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 11
acagagggaa aacgacacct                                           20

<210> SEQ ID NO 12
<211> LENGTH: 20
<212> TYPE: DNA
<213> ORGANISM: Artificial Sequence
<220> FEATURE:
<223> OTHER INFORMATION: Chemically Synthesized

```
<400> SEQUENCE: 12
aattttcact cgccgcttcg                                             20

<210> SEQ ID NO 13
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 13
gtgcactttt ataccgtctg ctt                                         23

<210> SEQ ID NO 14
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 14
cctgggcagg gagctaagat                                             20

<210> SEQ ID NO 15
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 15
tgtggtagag aagagctgg                                              19

<210> SEQ ID NO 16
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 16
agaagtgtgc caaggcact                                              19

<210> SEQ ID NO 17
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 17
tccttctcct ctttaactc                                              19

<210> SEQ ID NO 18
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 18
tgatgaagta caggtcggg                                              19

<210> SEQ ID NO 19
```

```
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 19
gaagttcgag ggcgacaccc                                               20

<210> SEQ ID NO 20
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 20
acaggccgat cacgtactgc                                               20

<210> SEQ ID NO 21
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 21
gagcaccagc agtacgtgat                                               20

<210> SEQ ID NO 22
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 22
cgtacatcta tgcgggctac                                               20

<210> SEQ ID NO 23
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 23
cgtgcggaaa tagaagcgcc                                               20
```

COMPOSITIONS AND METHODS FOR DECREASING, OR PREVENTING OR REVERSING GAIN OF, SKIN PIGMENTATION IN A MAMMALIAN SUBJECT

CROSS-REFERENCE TO RELATED APPLICATIONS

The present application is a continuation of, and claims priority to, U.S. application Ser. No. 15/562,725, filed Sep. 28, 2017, now issued as U.S. Pat. No. 11,236,074, which is a 35 U.S.C. § 371 national phase application from, and claims priority to, International Application No. PCT/US2016/026213, filed Apr. 6, 2016, and published under PCT Article 21(2) in English, which claims priority under 35 U.S.C. § 119(e) to U.S. Provisional Applications No. 62/143,597, filed Apr. 6, 2015, and No. 62/216,792, filed Sep. 10, 2015, all of which applications are incorporated herein by reference in their entireties.

STATEMENT REGARDING FEDERALLY SPONSORED RESEARCH OR DEVELOPMENT

This invention was made with government support under CA163566 awarded by National Institutes of Health/National Cancer Institute, and under CA174523 awarded by National Institutes of Health SPORE. The government has certain rights in the invention.

BACKGROUND OF THE INVENTION

Human skin color ranges in variety from the darkest brown to the lightest pinkish-white hues. Skin pigmentation in humans evolved primarily to regulate the amount of ultraviolet (UV) radiation penetrating the skin, thus controlling the radiation's biochemical effects. The most important substance that affects the actual skin color of humans is the pigment melanin.

Melanin controls the amount of UV radiation from the sun that penetrates the skin by absorption. While UV radiation can assist in the production of vitamin D, excessive exposure to UV can damage health. Melanin is produced within the skin in cells called melanocytes, and is the main determinant of the skin color of darker-skinned humans. Both the amount and type of melanin produced is controlled by a number of genes that operate under incomplete dominance. Melanocytes residing in the basal epidermis control human skin color through synthesis of melanin (melanogenesis), a complex process thought to be primarily regulated by alpha-melanocyte stimulating hormone (αMSH). The αMSH peptide is secreted centrally by the pituitary, and locally by surrounding keratinocytes in response to UV damage. αMSH binding to the melanocortin receptor 1 (MC1R), a G protein-coupled receptor (GPCR), activates adenylate cyclase, and increases cytosolic cAMP. This secondary messenger activates a cascade of downstream transcriptional events leading to expression of genes required for melanin synthesis.

Melanogenesis takes place within small membrane-bound packages called melanosomes. As the melanosomes become full of melanin, they move into the slender arms of melanocytes, from where they are transferred to the keratinocytes. Under normal conditions, melanosomes cover the upper part of the keratinocytes and protect them from genetic damage. One melanocyte supplies melanin to about 36 keranocytes according to signals from the keranocytes. They also regulate melanin production and replication of melanocytes. People have different skin colors mainly because their melanocytes produce different amount and kinds of melanin. The genetic mechanism behind human skin color is mainly regulated by the enzyme tyrosinase, which creates the color of the skin, eyes, and hair shades. Differences in skin color are also attributed to differences in size and distribution of melanosomes in the skin.

Uneven pigmentation of some sort affects most people, regardless of bioethnic background or skin color. Skin may appear lighter or darker than normal, or lack pigmentation at all. There may be blotchy and uneven areas, patches of brown to gray discoloration, or freckling. Apart from blood-related conditions such as jaundice, carotenosis, or argyria, skin pigmentation disorders generally occur because the body produces either too much or too little melanin.

There is a need in the art to develop novel compositions and methods for decreasing, or preventing or reversing gain of, skin pigmentation in a mammalian subject, such as a human. Such compositions and methods would be useful, in non-limiting embodiments, for treating or preventing skin disorders or diseases associated with hyperpigmentation. Such compositions and methods would be useful, in non-limiting embodiments, for treating or preventing skin disorders or diseases associated with pregnancy. The present invention fulfills this need.

BRIEF SUMMARY OF THE INVENTION

The invention provides a compound, or a salt, solvate, tautomer, enantiomer or diastereoisomer thereof. The invention further provides a pharmaceutical composition comprising at least one pharmaceutically acceptable carrier and at least one compound of the invention. The invention further provides a method of decreasing, or preventing or reversing gain of, skin pigmentation in a mammalian subject. The invention further provides a kit for decreasing, or preventing or reversing gain of, skin pigmentation in a mammalian subject.

In certain embodiments, the compound or molecule of the invention is

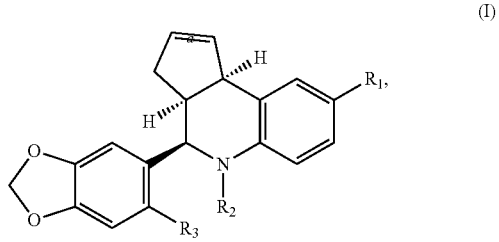

(I)

wherein: $R_1$ is selected from the group consisting of H and $C_1$-$C_3$ alkyl; $R_2$ is selected from the group consisting of H and $C_1$-$C_3$ alkyl; bond a is a single or double bond; $R_3$ is selected from the group consisting of H and halo.

In certain embodiments, the compound or molecule, or a salt, solvate, tautomer, enantiomer or diastereoisomer thereof, is G-15 (rel-(3aS,4S,9bR)-4-(6-bromobenzo[d][1,3]dioxol-5-yl)-3a,4,5,9b-tetrahydro-3H-cyclopenta[c]quinoline). In other embodiments, the compound or molecule, or a salt, solvate, tautomer, enantiomer or diastereoisomer thereof, is not G-15.

In certain embodiments, the compound or molecule, or a salt, solvate, tautomer, enantiomer or diastereoisomer thereof, is G-36 (rel-(3 aS,4R,9bR)-4-(6-bromobenzo[d][1,3]dioxol-5-yl)-8-isopropyl-3a,4,5,9b-tetrahydro-3H-cyclopenta[c]quinolone). In other embodiments, the compound or molecule, or a salt, solvate, tautomer, enantiomer or diastereoisomer thereof, is not G-36.

In certain embodiments, the compound or molecule, or a salt, solvate, tautomer, enantiomer or diastereoisomer thereof, is CH2P4 (rel-(8S,9S,10S,13S,14S,17S)-17-acetyl-13-methyl-10-vinyl-6,7,8,9,10,11,12,13,14,15,16,17-dodecahydro-1H-cyclopenta[a]phenanthren-3(2H)-one). In other embodiments, the compound or molecule, or a salt, solvate, tautomer, enantiomer or diastereoisomer thereof, is not CH2P4.

In certain embodiments, in (I) $R_1$ is H or 2-propyl. In other embodiments, in (I) $R_2$ is H or methyl. In yet other embodiments, in (I) bond a is a double bond. In yet other embodiments, in (I) bond a is a single bond. In yet other embodiments, $R_3$ is selected from the group consisting of H, F, Cl, and Br.

In certain embodiments, the compound is at least one selected from the group consisting of:

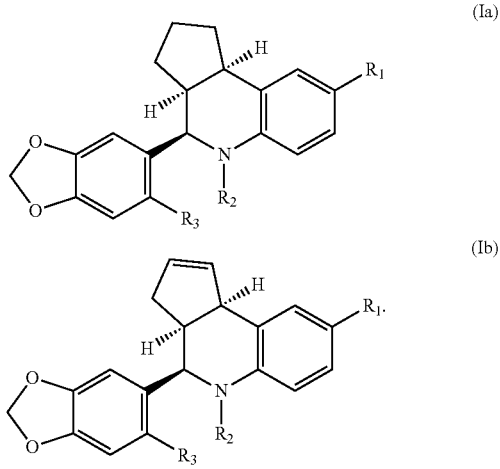

In certain embodiments, the pharmaceutical composition is formulated for topical or transdermal administration. In other embodiments, the pharmaceutical composition does not comprise G-15. In yet other embodiments, the pharmaceutical composition does not comprise G-36. In yet other embodiments, the pharmaceutical composition does not comprise CH2P4. In yet other embodiments, the pharmaceutical composition further comprises at least one sun-blocking agent. In yet other embodiments, the pharmaceutical composition further comprises at least one sunscreen lotion.

In certain embodiments, the method comprises administering to the subject a therapeutically effective amount of at least one compound selected from the group consisting of: (i) a GPER antagonist that does not bind to a canonical nuclear estrogen receptor, and (ii) a PAQR7 agonist that does not bind to a canonical nuclear progesterone receptor.

In certain embodiments, the subject is human.

In certain embodiments, the canonical nuclear estrogen receptor comprises at least one selected from the group consisting of ERα and ERβ.

In certain embodiments, the canonical nuclear progesterone receptor comprises at least one selected from the group consisting of PR-A and PR-B.

In certain embodiments, the compound is a GPER1 antagonist.

In certain embodiments, the subject is suffering from at least one condition selected from the group consisting of pigmentary changes associated with oral contraceptive use, pregnancy, and endogenous estrogens in females; solar lentigo; acne; eczema; chemical, sun, and thermal burn scars; lupus; psoriasis; sarcoidosis; pityriasis; erythema dyschromicum perstans; blistering diseases; drug reactions; lichen planus; and other inflammatory skin insults.

In certain embodiments, the compound is administered topically or transdermally to the subject. In yet other embodiments, the compound is formulated as a pharmaceutical composition for topical or transdermal administration. In yet other embodiments, the pharmaceutical composition further comprises at least one sun-blocking agent. In yet other embodiments, the pharmaceutical composition further comprises a sunscreen lotion. In yet other embodiments, the pharmaceutical composition is essentially free of a skin bleaching agent.

In certain embodiments, the compound is at least one selected from the group consisting of G-15, G-36 and CH2P4.

In certain embodiments, the kit comprises at least one compound and/or pharmaceutical composition of the invention. In other embodiments, the kit further comprises instructions for topically or transdermally administering the at least one pharmaceutical composition to the subject.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2A comprises a schematic illustration of classical regulation of human melanocyte homeostasis. FIG. 2B comprises a bar graph illustrating melanin production in response to αMSH in a dose dependent manner. FIG. 2C comprises a bar graph illustrating melanin production in response to estrogen in a dose dependent manner. FIG. 2D comprises a bar graph illustrating melanin production by melanocytes treated with vehicle, αMSH, or estrogen. FIG. 2E comprises a bar graph illustrating melanin production in response to progesterone (P4) in a dose dependent manner. FIG. 2F comprises a bar graph illustrating melanin production in response to estrogen and progesterone using iPS-derived female melanocytes. FIG. 2G comprises a bar graph illustrating melanin production in response to estrogen and progesterone using facial, aged-adult melanocytes. N=3 biologic replicates for each experiment. Error bars denote ±s.d., *p<0.05.

FIGS. 3A-3F comprise a set of images and bar graphs illustrating the finding that estrogen and progesterone reciprocally regulate melanin synthesis. FIG. 3A comprises a bar graph illustrating melanin content of primary human melanocytes treated with estrogen (E2), compared to vehicle-treated controls. FIG. 3B comprises a bar graph and images illustrating Fontana-Masson (melanin) staining of organotypic skin treated with vehicle or estrogen. Relative melanin content is illustrated in the bar graph at the bottom of the Figure. FIG. 3C comprises a bar graph and images illustrating MITF (microphthalmia-associated transcription factor) immunohistochemistry of organotypic skin treated with vehicle or estrogen. Melanocyte population density is illustrated in the bar graph at the bottom of the Figure. FIG. 3D comprises a bar graph illustrating melanin content of primary human melanocytes treated with progesterone (P4), compared to vehicle. FIG. 3E comprises a bar graph and images illustrating Fontana-Masson (melanin) staining of organotypic skin tissues treated with progesterone or vehicle. Relative melanin content is illustrated in the bar graph at the bottom of the Figure. FIG. 3F comprises a bar graph and images illustrating MITF immunohistochemistry of organotypic skin tissues treated with vehicle or progesterone. Melanocyte population density is illustrated in the bar graph at the bottom of the Figure. N=3 biologic replicates for each experiment. Error bars denote ±s.d., *p<0.05, scale bar=50 μm.

FIG. 4A comprises a bar graph illustrating cAMP ELISA from estrogen-treated melanocytes. FIG. 4B comprises a set of western blot images demonstrating changes in classical melanin pathway regulators after estrogen treatment. FIG. 4C comprises a bar graph illustrating cAMP ELISA from progesterone-treated melanocytes. FIG. 4D comprises a set of western blot images demonstrating changes in classical melanin pathway regulators after progesterone treatment. FIG. 4E comprises a bar graph illustrating a melanin assay from melanocytes treated with estrogen and progesterone simultaneously. FIG. 4F comprises a set of western blot images for estrogen and progesterone receptors in MCF7 cells and melanocytes. FIG. 4G comprises a bar graph illustrating melanin content of melanocytes transduced with control shRNA or shRNA targeting GPER. Cells were treated with either vehicle or estrogen. FIG. 4H comprises a bar graph illustrating a melanin assay performed on melanocytes transduced with control shRNA or shRNA targeting PAQR7. Cells were treated with either vehicle or progesterone. N=3 biologic replicates for each experiment. Error bars denote ±s.d., *p<0.05.

FIGS. 5A-5H comprises a set of bar graphs and table illustrating hormone receptors in melanocytes. FIG. 5A comprises a bar graph illustrating relative gene expression of classical hormone receptors in MCF7 cells and melanocytes, as determined by qRT-PCR. Ct values were normalized to actin, and set relative to the expression of androgen receptor (AR) in MCF7 cells. FIG. 5B comprises a table illustrating RPKM values for classical and nonclassical estrogen and progesterone receptors in human melanocytes, by convention, RPKM values >1 indicate the gene is expressed. FIG. 5C comprises a bar graph illustrating expression of GPER and Progestin and AdipoQ Receptor 7 (PAQR7) displayed as 1/Ct value. FIG. 5D comprises a bar graph illustrating relative expression of GPER and PAQR7 transcripts in melanocytes, fibroblasts, and keratinocytes, as determined by qRT-PCR, displayed relative to the expression level in melanocytes. FIG. 5E comprises a bar graph illustrating qRT-PCR showing mRNA knockdown efficiency of the two hairpins targeting GPER. FIG. 5F comprises a bar graph illustrating qRT-PCR showing mRNA knockdown efficiency of the two hairpins targeting PAQR7. FIG. 5G comprises a set of bar graphs illustrating melanin content of melanocytes transduced with LentiCRISPRV2 with guide RNA targeting GFP or GPER. Cells were treated with either vehicle or estrogen. FIG. 5H comprises a set of bar graphs illustrating melanin content of melanocytes transduced with LentiCRISPRV2 with guide RNA targeting GFP or PAQR7. Cells were treated with either vehicle or progesterone. Error bars denote ±s.d., *p<0.05.

FIG. 7A is a bar graph illustrating melanin production in response to tamoxifen (TMX). FIG. 7B is a bar graph illustrating melanin production in response to ethinyl estradiol (EE2). N=3 biologic replicates for each experiment. Error bars denote ±s.d., *p<0.05.

FIG. 9A comprises a bar graph illustrating melanin production in response to CH2P4, a specific PAQR7 agonist. FIG. 9B comprises a bar graph illustrating melanin assay performed on melanocytes lentivirally transduced with control shRNA or shRNA targeting PAQR7. These cells were treated with either vehicle or CH2P4. N=3 biologic replicates for each experiment. Error bars denote ±s.d., *p<0.05.

FIG. 10A comprises a set of images illustrating organotypic skin treated with vehicle (left) or CH2P4 (right). FIG. 10B comprises a set of images and bar graph illustrating Fontana-Masson (melanin) staining of organotypic skin treated with vehicle or CH2P4. Quantification of melanin content is illustrated on the right. FIG. 10C comprises a set of images and bar graph illustrating MITF immunohistochemistry of organotypic skin treated with vehicle or CH2P4. Quantification of melanocyte population density is illustrated on the right. N=3 biologic replicates for each experiment. Error bars denote ±s.d., *p<0.05, scale bar=50 μm.

DETAILED DESCRIPTION OF THE INVENTION

The present invention relates, in one aspect, to the unexpected discovery that compounds of the invention modulate skin pigmentation in a mammalian subject, such as a human. In certain embodiments, the compounds of the invention treat or prevent skin hyperpigmentation in a subject. In other embodiments, the compounds of the invention treat or prevent wrinkles and/or discolorations of premature aging. In yet other embodiments, the compositions of the invention modulate skin color for esthetic benefit without exposure to skin bleaching products and/or DNA-damaging UV radiation. In yet other embodiments, the compositions of the invention help revert or minimize estrogen-associated skin changes (such as, for example, darkening of the skin, appearance of skin spots, and the like), which may take place for example during pregnancy and/or during therapeutic treatment with estrogen or analogs thereof.

Human pregnancy and oral contraceptive use are commonly associated with altered epidermal pigmentation, and this suggests that changes in circulating hormones may regulate melanocyte homeostasis. However, the specific hormones, receptors, and downstream pathways mediating these effects have been undefined.

As demonstrated herein, physiologically relevant levels of 17β-estradiol (estrogen) promotes skin pigment production, while progesterone has opposing effects. Altered melanin production is associated with parallel changes in cAMP, a known regulator of mammalian pigmentation. Normal primary melanocytes do not express the classical estrogen and progesterone receptors (ER/PR). The present studies demonstrate that melanocytes express the non-canonical steroid hormone receptors G protein-coupled estrogen receptor 1 (GPER1), and Progestin and AdipoQ Receptor 7 (PAQR7). Lentiviral-mediated CRISPR-Cas9 ablation of these proteins blocks the pigmentary effects of estrogen and progesterone, suggesting that estrogen and progesterone reciprocally affect pigmentation through the non-canonical receptors GPER1 and PAQR7, respectively, to regulate human melanocyte homeostasis. In certain aspects, modulation of these receptors and their associated signaling pathway elements have therapeutic utility in disorders of epidermal pigmentation.

Figure 11:
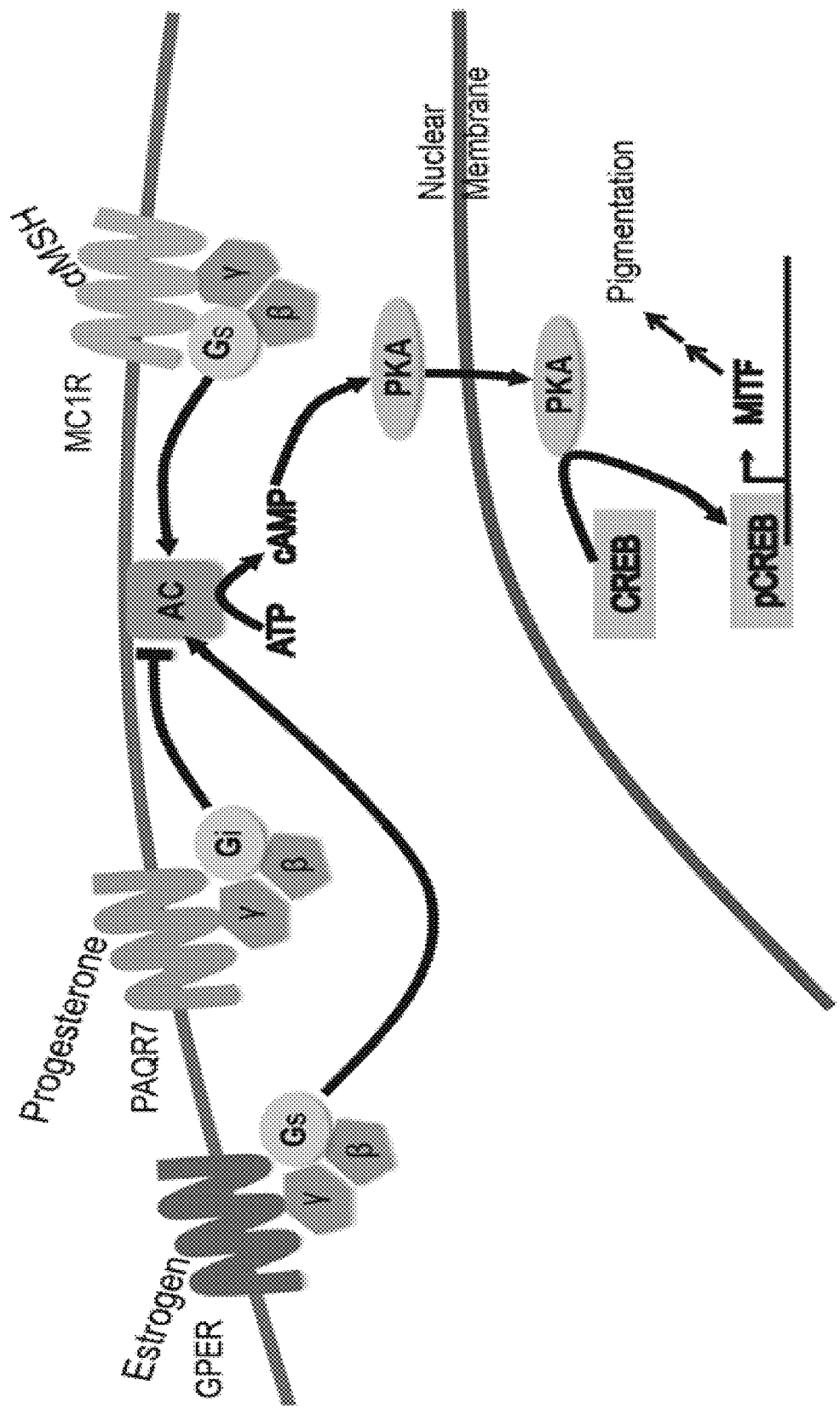
FIG. 11 comprises a schematic representation of selected biological pathways discussed herein.

The results presented herein, utilizing both genetic depletion and specific pharmacologic agonists and antagonists, establish that estrogen and progesterone influence human melanocyte pigment production through activation of the nonclassical hormone receptors GPER and PAQR7, respectively (FIG. 11). In one non-limiting aspect, specific activation of these receptors using selective agonist or antagonists is sufficient to increase or decrease pigment synthesis, avoiding the potentially undesirable effects of classical estrogen and progesterone receptor activation in other cell types. GPER and PAQR7 have reduced expression in keratinocytes or fibroblasts, which should limit drug effects to the cells of interest, in contrast to forskolin, which nonspecifically activates adenylate cyclase in all cells.

In non-limiting embodiments, G-15 and G-36 are GPER antagonists, and do not bind to a canonical nuclear ER. In certain embodiments, the canonical nuclear ER comprises ERα and/or ERβ.

In non-limiting examples, CH2P4 is a PAQR7 agonist and does not bind to a canonical nuclear PR. In certain embodiments, the canonical nuclear PR comprises PR-A and/or PR-B.

In one aspect, specific GPER antagonists and PAQR7 agonists represent a useful, novel class of therapeutics for normalizing disorders of epidermal pigmentation. Myriad genetic and acquired conditions including common afflictions, such as acne, eczema, vitiligo, ultraviolet (UV) radiation exposure, traumatic injury, and pregnancy, are associated with alterations in skin pigmentation that can be extensive and long-lasting.

In certain non-limiting embodiments, targeting the receptor(s) described herein can protect skin from wrinkles, and discolorations of premature aging, and also modulate skin color for esthetic benefit without exposure to DNA-damaging UV radiation or toxic skin bleaching agents.

The invention should not be construed to be limited to the compounds, or any analog thereof, recited herein. In certain embodiments, the present invention encompasses any compounds that act as antagonists towards GPER and do not bind to the canonical nuclear estrogen receptor. In other embodiments, the present invention encompasses any compounds that act as agonists towards PAQR7 and do not bind to the canonical nuclear progesterone receptor.

Definitions

As used herein, each of the following terms have the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics and chemistry are those well-known and commonly employed in the art.

As used herein, the term "19-CH2P4" or "CHP4" refers to rel-(8S,9S,10S,13 S,14S,17S)-17-acetyl-13-methyl-10-vinyl-6,7,8,9,10,11,12,13,14,15,16,17-dodecahydro-1H-cyclopenta[a]phenanthren-3(2H)-one), or a salt, solvate, enantiomer or diastereoisomer thereof.

As used herein, the articles "a" and "an" refer to one or to more than one (i.e., to at least one) of the grammatical object of the article. By way of example, "an element" means one element or more than one element.

As used herein, the term "αMSH" refers to alpha-melanocyte stimulating hormone.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, ±5%, ±1%, or ±0.1% from the specified value, as such variations are appropriate to perform the disclosed methods.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or isopropoxy) and the higher homologs and isomers. A specific example is ($C_1$-$C_3$)alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific embodiment is ($C_1$-$C_4$)alkyl, such as, but not limited to, ethyl, methyl, isopropyl, n-butyl, isobutyl, t-butyl, and cyclopropylmethyl.

As used herein, the term "AR" refers to androgen receptor.

As used herein, the term "cAMP" refers to cyclic adenosine monophosphate.

As used herein, the term "CREB" refers to cAMP response element-binding protein.

A "disease" is a state of health of an animal wherein the animal cannot maintain homeostasis, and wherein if the disease is not ameliorated, the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "E2" refers to estrogen.

As used herein, the term "EE2" refers to ethinyl estradiol.

As used herein, the terms "effective amount" or "therapeutically effective amount" or "pharmaceutically effective amount" of a compound are used interchangeably to refer to the amount of the compound sufficient to provide a beneficial effect to the subject to which the compound is administered.

As used herein, the term "ER" refers to estrogen receptor.

As used herein, the term "GPCR" refers to a G protein-coupled receptor.

As used herein, the term "G15" or "G-15" refers to rel-(3aS,4R,9bR)-4-(6-bromobenzo[d][1,3]dioxol-5-yl)-2,3,3a,4,5,9b-hexahydro-1H-cyclopenta[c]quinolone, or a salt, solvate, enantiomer or diastereoisomer thereof.

As used herein, the term "G36" or "G-36" refers to rel-(3aS,4R,9bR)-4-(6-bromobenzo[d][1,3]dioxol-5-yl)-8-isopropyl-3a,4,5,9b-tetrahydro-3H-cyclopenta[c]quinolone), or a salt, solvate, enantiomer or diastereoisomer thereof.

As used herein, the term "GPR30 receptor" (also known as GPER1; CEPR; CMKRL2; DRY12; FEG-1; GPCR-Br; GPER; LERGU; LERGU2; LyGPR; or mER) refers to a 7-transmembrane (7TM) G protein-coupled receptor that mediate estrogen-dependent signal transduction. GPR30 is an intracellular protein, found in the endoplasmic reticulum, which binds estrogen with high affinity ($K_d$ of 6 nM) and mediates rapid cellular responses including calcium mobilization and phosphatidylinositol 3,4,5-trisphosphate production in the nucleus. GPR30 receptor refers to all types of GPR30 receptor, regardless of the tissue in which such receptor is found and refers to any variant thereof, including receptors of mammals (such as humans and domesticated mammals where veterinary applications are relevant) and variants thereof. Other names which have been used for GPR30 include CMKRL2, DRY12, FEG-1, GPCR-Br, LERGU, LERGU2, LyGPR, CEPR and MGC99678, among others.

As used herein, the term "halo" or "halogen" alone or as part of another substituent refers to, unless otherwise stated, a fluorine, chlorine, bromine, or iodine atom.

As used herein, an "instructional material" includes a publication, a recording, a diagram, or any other medium of expression that can be used to communicate the usefulness of a compound, composition, assay or method of the invention in a kit for suppressing or reducing systemic immune response in a subject. The instructional material of the kit of the invention can, for example, be affixed to a container which contains the identified compound, composition, assay, or methods of the invention or be shipped together with a container that contains the identified compound, composition, assay, or method. Alternatively, the instructional material can be shipped separately from the container with the intention that the instructional material and the compound, composition, assay, or method be used cooperatively by the recipient.

As used herein, the term "MC1R" refers to melanocortin receptor 1.

As used herein, the term "MITF" refers to microphthalmia-associated transcription factor.

As used herein, the term "modulate" means, with respect to disease states or conditions associated with binding of a compound of the present invention to a receptor contemplated in the present invention, to produce, either directly or indirectly, an improvement or lessening of a condition or disease state which was, prior to administration of a compound according to the present invention, sub-optimal and in many cases, debilitating and even life threatening. Modulation may occur by virtue of agonist activity, antagonist activity or mixed agonist/antagonist activity (depending on the receptor site).

As used herein, the term "P4" refers to progesterone.

"Parenteral" administration of a composition includes, e.g., subcutaneous (s.c.), intravenous (i.v.), intramuscular (i.m.), or intrasternal injection, or infusion techniques.

As used herein, the term "PAQR7" refers to Progestin and AdipoQ Receptor 7.

As used herein, the term "pharmaceutical composition" or "composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary, intracranial, transdermal and topical administration. In certain embodiments, the administration comprises topical administration.

As used herein, the term "pharmaceutically acceptable" refers to a material, such as a carrier or diluent, which does not abrogate the biological activity or properties of the composition, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and/or bases, including inorganic acids, inorganic bases, organic acids, inorganic bases, solvates (including hydrates) and clathrates thereof.

As used herein, a "pharmaceutically effective amount," "therapeutically effective amount" or "effective amount" of a compound is that amount of compound that is sufficient to provide a beneficial effect to the subject to which the compound is administered.

As used herein, the term "PR" refers to progesterone receptor.

The term "prevent," "preventing" or "prevention" as used herein means avoiding or delaying the onset of symptoms associated with a disease or condition in a subject that has not developed such symptoms at the time the administering of an agent or compound commences. Disease, condition and disorder are used interchangeably herein.

By the term "specifically bind" or "specifically binds" as used herein is meant that a first molecule preferentially binds to a second molecule (e.g., a particular receptor or enzyme), but does not necessarily bind only to that second molecule.

As used herein, the terms "subject" and "individual" and "patient" can be used interchangeably and may refer to a human or non-human mammal or a bird. Non-human mammals include, for example, livestock and pets, such as ovine, bovine, porcine, canine, feline and murine mammals. In certain embodiments, the subject is human.

As used herein, the term "TMX" refers to tamoxifen.

As used herein, "topical administration" or "topical application" refers to a medication applied to body surfaces such as the skin or mucous membranes.

The term to "treat," as used herein, means reducing the frequency with which symptoms are experienced by a patient or subject or administering an agent or compound to reduce the severity with which symptoms are experienced. An appropriate therapeutic amount in any individual case may be determined by one of ordinary skill in the art using routine experimentation.

As used herein, the term "treatment" or "treating" is defined as the application or administration of a therapeutic agent, i.e., a composition useful within the invention (alone or in combination with another pharmaceutical agent), to a subject, or application or administration of a therapeutic agent to an isolated tissue or cell line from a subject (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder or the potential to develop the disease or disorder. Such treatments may be specifically tailored or modified, based on knowledge obtained from the field of pharmacogenomics.

As used herein, the term "UV" refers to ultraviolet.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds and Compositions

In one aspect, the present invention encompasses a compound that binds to PAQR7, and does not bind to a canonical nuclear progesterone receptor (PR). In certain embodiments, the compound is a PAQR7 agonist.

In certain embodiments, the compound of the invention, or a salt, solvate, tautomer, enantiomer or diastereoisomer thereof, is CH2P4 (also known as 19-CH2P4; rel-(8S,9S, 10S,13 S,14S,17S)-17-acetyl-13-methyl-10-vinyl-6,7,8,9, 10,11,12,13,14,15,16,17-dodecahydro-1H-cyclopenta[a] phenanthren-3 (2H)-one):

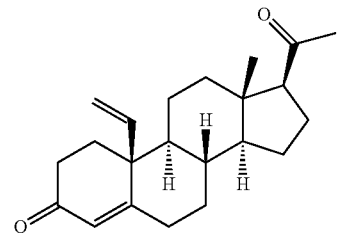

In another aspect, the present invention encompasses an estrogen derivative or analog thereof, that binds to GPER, such as but not limited to GPER1, and does not bind to a canonical nuclear estrogen receptor (ER). In certain embodiments, the estrogen derivative or analog is a GPER antagonist.

In certain embodiments, the compound of the invention, or a salt, solvate, tautomer, enantiomer or diastereoisomer thereof, is at least one molecule of formula (I):

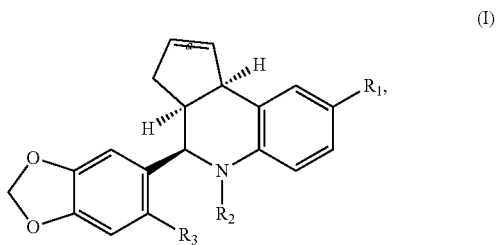

(I)

wherein: $R_1$ is selected from the group consisting of H and $C_1$-$C_3$ alkyl; $R_2$ is selected from the group consisting of H and $C_1$-$C_3$ alkyl; bond a is a single or double bond; $R_3$ is selected from the group consisting of H and halo;

In certain embodiments, the compound is not G-15. In other embodiments, the compound is not G-36. In yet other embodiments, the compound is not G-15 or G-36.

In certain embodiments, $R_1$ is selected from the group consisting of H, methyl, ethyl, 1-propyl, and 2-propyl. In other embodiments, $R_2$ is H or 2-propyl.

In certain embodiments, bond a is a double bond. In other embodiments, bond a is a single bond.

In certain embodiments, $R_2$ is selected from the group consisting of H, methyl, ethyl, 1-propyl and 2-propyl. In certain embodiments, $R_2$ is H.

In certain embodiments, $R_3$ is selected from the group consisting of H, F, Cl, Br and I. In certain embodiments, $R_3$ is Br.

In certain embodiments, the compound is at least one selected from the group consisting of:

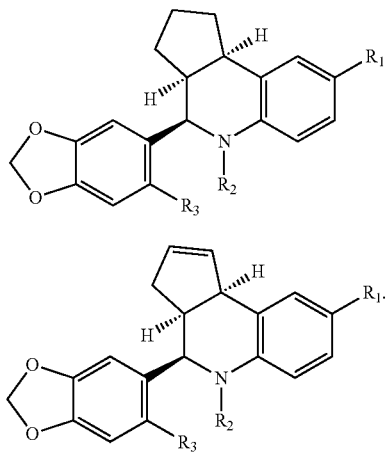

In certain embodiments, the compound is at least one selected from the group consisting of:

G15 or G-15 (rel-(3aS,4S,9bR)-4-(6-bromobenzo[d][1,3]dioxol-5-yl)-3a,4,5,9b-tetrahydro-3H-cyclopenta[c]quinoline):

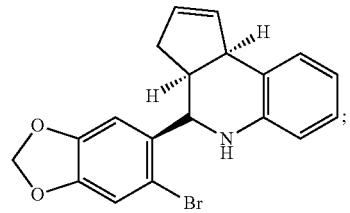

G36 or G-36 (rel-(3aS,4R,9bR)-4-(6-bromobenzo[d][1,3]dioxol-5-yl)-8-isopropyl-3a,4,5,9b-tetrahydro-3H-cyclopenta[c]quinolone):

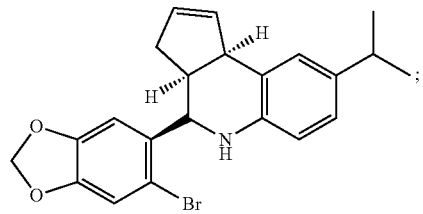

rel-1-(2-((3aS,4S,9bR)-4-(6-bromobenzo[d][1,3]dioxol-5-yl)-3a,4,5,9b-tetrahydro-3H-cyclopenta[c]quinolin-8-yl)ethyl)-3-(3-iodophenyl)urea (described in Ramesh, et al., 2010, J. Med. Chem. 53:1004-1014):

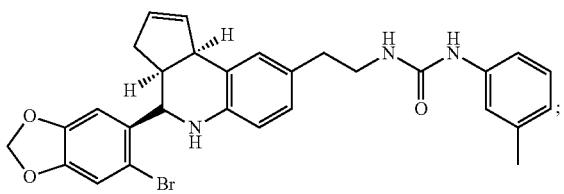

rel-(3aS,4S,9bR)-4-(6-bromobenzo[d][1,3]dioxol-5-yl)-8-((E)-1-(2-(5-iodopyridin-2-yl)hydrazono)ethyl)-3a,4,5,9b-tetrahydro-3H-cyclopenta[c]quinoline (described in Ramesh, et al., 2010, J. Med. Chem. 53:1004-1014):

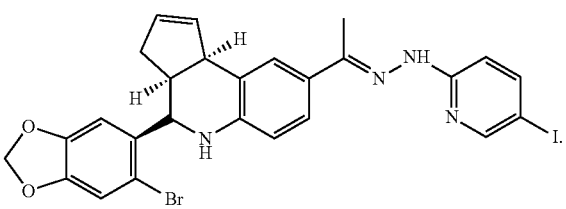

In certain embodiments, the compound useful within the methods of the invention, or a salt, solvate, enantiomer or diastereoisomer thereof, is at least one GPER antagonist recited in U.S. Patent Application Publications No. 2008/0167334 and US 2011/0092533, all of which are incorporated herein in their entireties by reference:

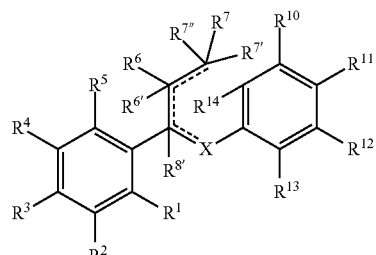

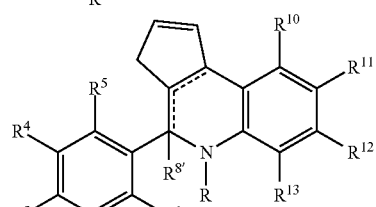

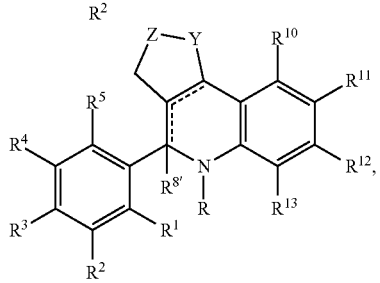

wherein:
- X is =N—, O, S, or N—R, with the proviso that when X is N—R and R is a bond, N together with $R^1$ forms a 5- to 7-membered optionally substituted heterocyclic group;
- R is a bond, H, OH, $NO_2$, optionally substituted $C_1$-$C_6$ hydrocarbyl (such as optionally substituted alkyl), optionally substituted aryl, optionally substituted heteroaryl, optionally substituted heterocycle, optionally substituted —C(O)—($C_1$-$C_6$) alkyl (amide), optionally substituted —C(O)—O—($C_1$-$C_6$) alkyl (urethane), optionally substituted —C(O)—NH($C_1$-$C_6$) alkyl (urea), optionally substituted —C(O)—N($C_1$-$C_6$)dialkyl, optionally substituted —C(O)—NH(aryl), optionally substituted —C(O)—N(diaryl), optionally substituted —C(O)—NH(heteroaryl), optionally substituted —C(O)—N(diheteroaryl), optionally substituted —C(O)—NH(heterocycle) or optionally substituted —C(O)—N(diheterocycle);
- $R^1$, $R^2$ and $R^5$ are each independently selected from H, OH, $NO_2$, halogen, $C_1$-$C_6$ optionally substituted carboxylic acid group, optionally substituted O—($C_1$-$C_6$) alkyl, optionally substituted $C_1$-$C_6$ hydrocarbyl, optionally substituted aryl, optionally substituted heteroaryl, optionally substituted heterocycle, optionally substituted —C(O)—($C_1$-$C_6$) alkyl (ketone), optionally substituted —C(O)—O—($C_1$-$C_6$) alkyl (ester), optionally substituted O—C(O)—($C_1$-$C_6$) alkyl (ester), optionally substituted —C(O)—NH($C_1$-$C_6$) alkyl (urea), optionally substituted —C(O)—N($C_1$-$C_6$)dialkyl, optionally substituted —C(O)—NH(aryl), optionally substituted —C(O)—N(diaryl), optionally substituted —C(O)—NH(heteroaryl), optionally substituted —C(O)—N(diheteroaryl), optionally substituted —C(O)—NH(heterocycle) or optionally substituted —C(O)—N(diheterocycle);
- $R^3$ and $R^4$ are each independently selected from H, OH, $NO_2$, halogen, $C_1$-$C_6$ optionally substituted carboxylic acid group, optionally substituted O—($C_1$-$C_6$)alkyl, optionally substituted $C_1$-$C_6$ hydrocarbyl, optionally substituted aryl, optionally substituted heteroaryl, optionally substituted heterocycle, optionally substituted —C(O)—($C_1$-$C_6$) alkyl (ketone), optionally substituted —C(O)—O—($C_1$-$C_6$) alkyl (ester), optionally substituted O—C(O)—($C_1$-$C_6$) alkyl (ester), optionally substituted —C(O)—NH($C_1$-$C_6$) alkyl (urea), optionally substituted —C(O)—N($C_1$-$C_6$)dialkyl, optionally substituted —C(O)—NH(aryl), optionally substituted —C(O)—N(diaryl), optionally substituted —C(O)—NH(heteroaryl), optionally substituted —C(O)—N(diheteroaryl), optionally substituted —C(O)—NH(heterocycle) or optionally substituted —C(O)—N(diheteroaryl) or $R^3$ and $R^4$ together form a 5- or 6-membered optionally substituted carbocyclic (which may be saturated or unsaturated), optionally substituted aryl, optionally substituted heteroaryl or optionally substituted heterocyclic group;
- $R^6$ and $R^7$ are each independently absent or are selected from H, OH, $NO_2$, halogen, $C_1$-$C_6$ optionally substituted carboxylic acid group, optionally substituted O—($C_1$-$C_6$)alkyl, optionally substituted $C_1$-$C_6$ hydrocarbyl, optionally substituted aryl, optionally substituted heteroaryl, optionally substituted heterocycle, optionally substituted —C(O)—($C_1$-$C_6$) alkyl (ketone), optionally substituted —C(O)—O—($C_1$-$C_6$) alkyl (ester), optionally substituted O—C(O)—($C_1$-$C_6$) alkyl (ester), optionally substituted —C(O)—NH($C_1$-$C_6$) alkyl (urea), optionally substituted —C(O)—N($C_1$-$C_6$) dialkyl, optionally substituted —C(O)—NH(aryl), optionally substituted —C(O)—N(diaryl), optionally substituted —C(O)—NH(heteroaryl), optionally substituted —C(O)—N(diheteroaryl), optionally substituted —C(O)—NH(heterocycle) or optionally substituted —C(O)—N(diheteroaryl), or together $R^6$ and $R^7$ form a 4-, 5-, 6- or 7-membered optionally substituted carbocyclic (which may be saturated or unsaturated), optionally substituted aryl, optionally substituted heteroaryl or optionally substituted heterocyclic group, or a 5- to 9-membered optionally substituted carbocyclic or heterocyclic bicyclic group, with the proviso that $R^7$ is not absent when both $R^{7'}$ and $R^{7''}$ are also absent;
- $R^{6'}$ is absent, H, $C_1$-$C_6$ optionally substituted hydrocarbyl group (such as H, $CH_3$ or $CH_2CH_3$) or together with $R^6$ forms =O;
- $R^{7'}$ is absent, H, optionally substituted hydrocarbyl group (such as H, $CH_3$ or $CH_2CH_3$), or together with $R^7$ forms =O;
- $R^{7''}$ is absent, H, OH, halogen, optionally substituted O—($C_1$-$C_6$)alkyl, optionally substituted $C_1$-$C_6$ hydrocarbyl, optionally substituted aryl, optionally substituted heteroaryl, optionally substituted heterocycle, optionally substituted —C(O)—($C_1$-$C_6$) alkyl (ketone), optionally substituted —C(O)—O—($C_1$-$C_6$) alkyl (ester), optionally substituted O—C(O)—($C_1$-$C_6$) alkyl (ester), optionally substituted —C(O)—NH($C_1$-$C_6$) alkyl (urea), optionally substituted —C(O)—N($C_1$-$C_6$) dialkyl, optionally substituted —C(O)—NH(aryl), optionally substituted —C(O)—N(diaryl), optionally substituted —C(O)—NH(heteroaryl), optionally substituted —C(O)—N(diheteroaryl), optionally substituted —C(O)—NH(heterocycle) or optionally substituted —C(O)—N(diheteroaryl);
- $R^{8'}$ is absent (when the carbon to which $R^{8'}$ is attached and the carbon to which $R^6$ is attached form an optional double bond), H, $CH_3$ or $CH_2CH_3$;
- $R^{10}$, $R^{11}$, $R^{12}$ and $R^{13}$ are each independently H, OH, $NO_2$, halogen, $C_1$-$C_6$ optionally substituted carboxylic acid group, optionally substituted O—($C_1$-$C_6$)alkyl, optionally substituted $C_1$-$C_6$ hydrocarbyl, optionally substituted aryl, optionally substituted heteroaryl, optionally substituted heterocycle, optionally substituted —C(O)—($C_1$-$C_6$) alkyl (ketone), optionally substituted —C(O)—O—($C_1$-$C_6$) alkyl (ester), optionally substituted O—C(O)—($C_1$-$C_6$) alkyl (ester), optionally substituted —C(O)—NH($C_1$-$C_6$) alkyl (urea), optionally substituted —C(O)—N($C_1$-$C_6$)dialkyl, optionally substituted —C(O)—NH(aryl), optionally substituted —C(O)—N(diaryl), optionally substituted —C(O)—NH(heteroaryl), optionally substituted —C(O)—N(diheteroaryl), optionally substituted —C(O)—NH(heterocycle) or optionally substituted —C(O)—N(diheteroaryl);
- $R^{14}$ is H, OH, $NO_2$, halogen, $C_1$-$C_6$ optionally substituted carboxylic acid group, optionally substituted O—($C_1$-$C_6$)alkyl, optionally substituted $C_1$-$C_6$ hydrocarbyl, optionally substituted aryl, optionally substituted heteroaryl, optionally substituted heterocycle, optionally substituted —C(O)—($C_1$-$C_6$) alkyl (ketone), optionally substituted —C(O)—O—($C_1$-$C_6$) alkyl (ester), optionally substituted O—C(O)—($C_1$-$C_6$) alkyl (ester), optionally substituted —C(O)—NH($C_1$-$C_6$) alkyl (urea), optionally substituted —C(O)—N($C_1$-$C_6$)dialkyl, optionally substituted —C(O)—NH(aryl), optionally substituted —C(O)—N(diaryl), optionally substituted —C(O)—NH(heteroaryl), optionally substituted —C(O)—N(diheteroaryl), optionally substituted —C(O)—NH(heterocycle) or optionally substituted —C(O)—N(diheterocycle) or together with the carbon to which $R^7$ is attached forms a 5-, 6- or 7-membered optionally substituted carbocyclic (which may be saturated or unsaturated), optionally substituted aryl, optionally substituted heteroaryl or optionally substituted heterocyclic ring;

Y is optionally substituted $(CH_2)_n$ group where n is 0, 1 or 2, optionally substituted =CH— group, a C=O group, O, S, optionally substituted N—$(C_1$-$C_6)$alkyl, optionally substituted N-aryl, optionally substituted N-heteroaryl, optionally substituted N-heterocycle, optionally substituted N—C(O)—$(C_1$-$C_6)$alkyl, optionally substituted N—C(O)-aryl, optionally substituted N—C(O)— heteroaryl, optionally substituted N—C(O)-heterocycle;

Z is optionally substituted $(CH_2)_n$ group where n is 1 or 2, optionally substituted =CH— group, a C=O group, O, S, optionally substituted N—$(C_1$-$C_6)$alkyl, optionally substituted N-aryl, optionally substituted N-heteroaryl, optionally substituted N-heterocycle, optionally substituted N—C(O)—$(C_1$-$C_6)$alkyl, optionally substituted N—C(O)-aryl, optionally substituted N—C(O)— heteroaryl, optionally substituted N—C(O)-heterocycle.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

In certain embodiments, the invention further provides pharmaceutical compositions comprising at least one compound of the invention and at least one pharmaceutically acceptable carrier. In other embodiments, the pharmaceutical composition is formulated for topical and/or transdermal application. Topical formulations of the compounds contemplated within the invention may be used for skin lightening, as well as for treating skin conditions or diseases associated with hyperpigmentation. These conditions or diseases include, but are not limited to, acne; eczema; chemical, sun, and thermal burn scars; lupus; psoriasis; sarcoidosis; pityriasis; erythema dyschromicum perstans; blistering diseases; drug reactions; lichen planus; or other inflammatory skin insults.

In certain embodiments, the invention provides topical formulations comprising at least one sun-blocking agent and at least one compound of the invention. In other embodiments, the topical formulation comprises a formulated sunblock or sunscreen lotion and at least one compound of the invention. In yet other embodiments, the at least one sun-blocking agent allows for protection against UV light damage caused by the natural sun light, and the one or more compounds of the invention allow for lightening of the skin. In yet other embodiments, the melanin production triggered by the at least one compound of the invention further protects the skin against UV light damage caused by the natural sun light. In yet other embodiments, the topical formulation protects against UV-induced skin damage and/or aging.

The present invention also pertains to kits useful within any of the methods of the invention described herein. Such kits comprise components useful in any of the methods described herein, including for example, compositions and methods for modulating skin pigmentation in a mammalian subject, such as a human, one or more containers (e.g., test tube, cell culture dish, cell culture plate, cell culture flask, cell culture bag) for containing a component of any of the embodiments of the invention described elsewhere herein, and instructional materials.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, O-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Methods

In one aspect, the invention includes a method of modulating skin pigmentation in a mammalian subject, such as a human. In certain embodiments, the method of the invention treats or prevents skin hyperpigmentation in the subject. In other embodiments, the method of the invention promotes skin lightening in the subject. In other embodiments, the compound is administered topically or transdermally to the subject.

In certain embodiments, the method comprises administering to the subject a therapeutically effective amount of a compound that binds to a non-classical hormone receptor present on a melanocyte and does not bind to a canonical sex steroid hormone receptor, such as the estrogen and/or progesterone receptor. In other embodiments, the non-classical hormone receptor comprises PAQR7. In other embodiments, the non-classical hormone receptor comprises GPER. In yet other embodiments, the non-classical hormone receptor comprises GPER1 (also known as GPR30). In yet other embodiments, the compound is a GPER antagonist and decreases, or prevents further gain of, skin pigmentation. In yet other embodiments, the compound is a PAQR7 agonist and decreases, or prevents further gain of, skin pigmentation.

In certain embodiments, the subject is suffering from a condition comprising at least one selected from the group consisting of pigmentary changes associated with oral contraceptive use, pregnancy, and endogenous estrogens in females (such as melasma and chloasma); solar lentigo; acne; eczema; chemical, sun, and thermal burn scars; lupus; psoriasis; sarcoidosis; pityriasis; erythema dyschromicum perstans; blistering diseases; drug reactions; lichen planus; or other inflammatory skin insults.

Formulations/Administration

The relative amounts of the active ingredient, the pharmaceutically acceptable carrier, and any additional ingredients in a pharmaceutical composition of the invention will vary, depending upon the identity, size, and condition of the subject treated. By way of example, the composition may comprise between about 0.005% and about 100% (w/w) of the active agent, or any fractions or multiples thereof.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions comprising a compound contemplated within the invention are formulated using one or more pharmaceutically acceptable excipients or carriers. In certain embodiments, the pharmaceutical compositions of the invention comprise a therapeutically effective amount of at least one compound contemplated within the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are included in the composition. Prolonged absorption of the injectable compositions may be brought about by including in the composition an agent which delays absorption, for example, aluminum monostearate or gelatin.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. In certain embodiments, the administration comprises topical administration. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, PA), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. An illustrative preservative is a combination of about 0.5% to 2.0% benzyl alcohol and 0.05% to 0.5% sorbic acid.

The composition may include an antioxidant and a chelating agent that inhibit the degradation of the compound. Selected antioxidants for some compounds are BHT, BHA, α-tocopherol and ascorbic acid in the exemplary range of about 0.01% to 0.3%, such as BHT in the range of 0.03% to 0.1% by weight by total weight of the composition. For example, the chelating agent is present in an amount of from 0.01% to 0.5% by weight by total weight of the composition. Illustrative chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition which may be detrimental to the shelf life of the formulation. While BHT and disodium edetate are illustrative antioxidant and chelating agent respectively for some compounds, other suitable and equivalent antioxidants and chelating agents may be substituted as would be known to those skilled in the art.

The composition comprising a compound contemplated within the invention can be administered to a mammal as frequently as several times daily, or it may be administered less frequently, such as once a day, once a week, once every two weeks, once a month, or even less frequently, such as once every several months or even once a year or less.

It is understood that the amount of compound dosed per day may be administered, in non-limiting examples, every day, every other day, every 2 days, every 3 days, every 4 days, or every 5 days. For example, with every other day administration, a 0.5-5 mg per day dose may be initiated on Monday with a first subsequent 0.5-5 mg per day dose administered on Wednesday, a second subsequent 0.5-5 mg per day dose administered on Friday, and so on. The frequency of the dose will be readily apparent to the skilled artisan and will depend upon any number of factors, such as, but not limited to, the type and severity of the disease being treated, the type and age of the animal, and so forth.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Such formulations may be applied to the skin directly or through the use of swabs, applicators, spatulas and the like, as well as in the form of transdermal patches. In certain embodiments, the patch minimizes loss of pharmaceuticals through washing, friction, scratching and/or rubbing of the skin. In other embodiments, the patch increases absorption of the pharmaceutical through the skin, while minimizing the exposure of the skin to the pharmaceutical.

Topically administrable formulations may, for example, comprise from about 0.005% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, U.S. Pat. No. 6,323,219).

In alternative embodiments, the pharmaceutical composition of the invention may be optionally combined with other ingredients such as adjuvants, anti-oxidants, chelating agents, surfactants, foaming agents, wetting agents, emulsifying agents, viscosifiers, buffering agents, preservatives, and the like. In other embodiments, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition of the invention should be applied in an amount effective to affect desired changes. As used herein, "amount effective" shall mean an amount sufficient to cover the region of skin surface where a change is desired. An active compound should be present in the amount of from about 0.0001% to about 15% by weight volume of the composition; or in an amount from about 0.0005% to about 5% of the composition; or in an amount of from about 0.005% to about 1% of the composition. Such compounds may be synthetically- or naturally derived.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for topical administration, such as liniments, lotions, oil-in-water or water-in-oil emulsions such as creams, ointments or pastes, transdermal patches, and solutions or suspensions that are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In certain embodiments of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Unless otherwise noted, all cell lines, biological materials, chemical materials, reagents and resins were obtained from commercial suppliers and used without purification.

Melanocyte Culture

Primary melanocytes were extracted from fresh discarded surgical human foreskin specimens. After overnight incubation in Dispase, the epidermis was separated from the dermis and treated with trypsin for 10 minutes. Cells were pelleted and plated on selective MC Medium 254 (Invitrogen) with Human Melanocyte Growth Supplement, and 1% penicillin and streptomycin. Lightly pigmented primary melanocytes were utilized for experiments assaying estrogen and GPER agonist effects, and heavily pigmented primary melanocytes were utilized for experiments assaying progesterone and PAQR7 effects in melanin production. Progesterone (P8783), 17β-Estradiol (E8875), and αMSH (M4135) were purchased from Sigma-Aldrich. G-15 (14673) and G-36 (14397) were purchased from Cayman Chemical. CH2P4 (2085) was purchased from Axon Medchem. Pertussis toxin was purchased from R&D systems (3097). These compounds were diluted to working stock solutions in Medium 254.

Melanin Assay $2 \times 10^5$ melanocytes were seeded uniformly on 6-well tissue culture plates. Cells were treated with vehicle controls, sex steroids, hormone derivatives, or pertussis toxin for 4 days. Cells were then trypsinized, counted, and spun down at 300×g for 5 minutes. The resulting cell pellet was solubilized in 1M NaOH, and boiled for 5 minutes. The optical density of the resulting solution was read at 450 nm using an EMax microplate reader (Molecular Devices). The absorbance was normalized to the number of cells in each sample, and relative amounts of melanin were set based on vehicle treated controls. For tissue melanin assays, tissue was weighed prior to boiling in 1M NaOH for 20 minutes. Samples were spun down to eliminate insoluble materials, and then the optical density of the sample was measured and normalized to the weight of tissue.

cAMP ELISA cAMP ELISA was performed on primary human melanocytes using the Cyclic AMP XP Assay Kit (Cell Signaling Technology, #4339) following manufacturer instructions.

Western Blot Analyses and Antibodies

Adherent cells were treated with 1 μM doses of E2 and P4 overnight, washed once with DPBS, and lysed with 1% NP-40 buffer (150 mM NaCl, 50 mM Tris, pH 7.5, 1 mM EDTA, and 1% NP-40) containing 1× protease inhibitors (Roche) and 1× phosphatase inhibitors (Roche). Lysates were quantified (Bradford assay), normalized, reduced, denatured (95° C.) and resolved by SDS gel electrophoresis on 4-15% Tris/Glycine gels (Bio-Rad). Resolved protein was transferred to PVDF membranes (Millipore) using a Semi-Dry Transfer Cell (Bio-Rad), blocked in 5% dry milk in TBS-T and probed with primary antibodies recognizing MITF (Cell Signaling Technology, #12590, 1:1000), pCREB (Cell Signaling Technology, #9198, 1:1000), CREB (Cell Signaling Technology, #9104, 1:1000), and β-Actin (Cell Signaling Technology, #3700, 1:4000). After incubation with the appropriate secondary antibody, proteins were detected using either Luminata Crescendo Western HRP Substrate (Millipore) or ECL Western Blotting Analysis System (GE Healthcare).

Melanin Staining

Formalin-fixed paraffin embedded tissue was sectioned at 5 uM and collected on superfrost plus slides (Fisher), and subjected to Fontana-Masson stain for melanin. Briefly, sections were deparaffinized, rehydrated, and incubated in the following solutions: 2.5% aqueous silver nitrate for 10 min, 0.1% aqueous gold chloride for 15 min, and 5% aqueous sodium thiosulfate for 5 min. Distilled deionized water was used for rinsing and incubations were done at room temperature except for silver nitrate at 60° C. Slides were counterstained with 0.1% nuclear fast red Kernechtrot for 5 min, dehydrated, cleared, and coverslipped using MM24 mounting media (Leica). All staining reagents were from Polyscientific R & D Corporation.

Immunohistochemistry

Formalin fixed paraffin embedded (FFPE) human skin tissue sections from organotypic tissue was stained for MITF protein expression using a primary antibody to MITF (Leica Biosystems, NCL-L-MITF, 1:15). Staining was performed following the manufacturer protocol for high temperature antigen unmasking technique for immunohistochemical demonstration on paraffin sections.

Quantification of Melanin Staining

Tissue sections from organotypic culture were stained using methods described elsewhere herein. In terms of quantitation, briefly, 20× photomicrograph images of representative tissue sections were taken using the Zeiss Axiophot microscope. Tiff files of the images were saved and transferred to Adobe PHOTOSHOP® where pixels corresponding to Fontana-Masson staining and epidermal counter stain were selected using the color selection tool. Images corresponding to the single specific color were then analyzed using FIJI (Image J) to determine the number of pixels in each sample. The numbers of pixels representing Fontana-Masson staining were normalized to the total amount epidermal counter staining. Final ratios Fontana-Masson staining in the epidermis were set relative to amount of staining in vehicle treated controls.

Quantitative RT/PCR mRNA was extracted from melanocytes according to the RNeasy Mini Kit protocol (Qiagen), and reverse transcribed to cDNA using the High Capacity RNA-to cDNA kit (Applied Biosystems). Quantitative PCR of the resulting cDNA was carried out using Power SYBR Green Master Mix (Applied Biosystems) and gene-specific primers, in triplicate, on a ViiA 7 Real-Time PCR System (Life Technologies).

The following primers were used for detection; B-Actin forward: 5'-CAT GTA CGT TGC TAT CCA GGC-3' (SEQ ID NO:1); B-Actin reverse: 5'-CTC CTT AAT GTC ACG CAC GAT-3' (SEQ ID NO:2); ER-A forward: 5'-AAA GGT GGG ATA CGA AAA GAC C-3' (SEQ ID NO:3); ER-A reverse: 5'-AGC ATC CAA CAA GGC ACT GA-3' (SEQ ID NO:4); ER-B forward: 5'-GGC TGC GAG AAA TAA CTG CC-3' (SEQ ID NO:5); ER-B reverse: 5'-AAT GCG GAC ACG TGC TTT TC-3' (SEQ ID NO:6); PGR forward: 5'-AGG TCT ACC CGC CCT ATC TC-3' (SEQ ID NO:7); PGR reverse: 5'-AGT AGT TGT GCT GCC CTT CC-3' (SEQ ID NO:8); AR forward: 5'-GTG CTG TAC AGG AGC CGA AG-3' (SEQ ID NO:9); AR reverse: 5'-GTC AGT CCT ACC AGG CAC TT-3' (SEQ ID NO:10); GPER forward: 5'-ACA GAG GGA AAA CGA CAC CT-3' (SEQ ID NO:11); GPER reverse: 5'-AAT TTT CAC TCG CCG CTT CG-3' (SEQ ID NO:12); PAQR7 forward: 5'-GTG CAC TTT TAT ACC GTC TGC TT-3' (SEQ ID NO:13); PAQR7 reverse: 5'-CCT GGG CAG GGA GCT AAG AT-3' (SEQ ID NO:14). Relative expression was determined using the 2-[delta][delta] Ct method followed by normalization to the AR receptor transcript levels in MCF7 cells.

Lentiviral Vectors

The following shRNAs were expressed from the GIPZ vector (Open Biosystems): shPAR7.3 (V3LHS_364596, 5'-TGT GGT AGA GAA GAG CTG G-3'; SEQ ID NO:15), shPAQR7.4 (V3LHS_364598, AGAAGTGTGC-CAAGGCACT; SEQ ID NO:16) shGPER.1 (V2LHS_132008, 5'-TCC TTC TCC TCT TTA ACT C-3'; SEQ ID NO:17), shGPER.3 (V3LHS_390319, 5'-TGA TGAAGT ACA GGT CGG G-3'; SEQ ID NO:18).

Guide RNAs were designed using software tools provided on the website www dot genome-engineering dot org/. Guide RNAs were subsequently cloned into lentiCRISPRv2 (Addgene #52961) according to the accompanying protocol. Guide RNA sequences are as follows: lentiCRISPR GFP, 5'-GAA GTT CGA GGG CGA CAC CC-3' (SEQ ID NO:19); lentiCRISPR GPER.1, 5'-ACAGGCCGAT-CACGTACTGC-3' (SEQ ID NO:20); lentiCRISPR GPER.2, 5'-GAG CAC CAG CAG TAC GTG AT-3' (SEQ ID NO:21); lentiCRISPR PAQR7.1, 5' CGT ACA TCT ATG CGG GCT AC-3' (SEQ ID NO:22); lentiCRISPR PAQR7.5, 5'-CGT GCG GAAATA GAA GCG CC-3' (SEQ ID NO:23).

Non-Limiting Exemplary Topical Treatment.

2% (w/v) compound is prepared in DMSO. 20 μL of this solution is applied daily to the right ear, with vehicle only applied to the left ear, of 4-week-old C57BL/6 mice. These studies are performed without inclusion/exclusion criteria, randomization, or blinding. Based on a two-fold anticipated effect, this experiment is performed with 3 biological replicates.

Statistical Analysis

* denotes a P-value of less than 0.05 in an unpaired, two-tailed Students T-Test.

Example 1: Preparation of 3-D Organotypic Skin Cultures

Organotypic skin grafts containing MCs were established using modifications to previously detailed methods (Ridky, et al., Nature Med. 2010, 16, 1450-1455; Chudnovsky, et al., Nature Gen. 2005, 37, 745-749). The Keratinocyte Growth Media (KGM) used for keratinocyte-only skin grafts was replaced with modified Melanocyte Xenograft Seeding Media (MXSM). MXSM is a 1:1 mixture of KGM, lacking cholera toxin, and Keratinocyte Media 50/50 (Gibco) containing 2% FBS, 1.2 mM calcium chloride, 100 nM Et-3 (endothelin 3), 10 ng/mL rhSCF (recombinant human stem cell factor), and 4.5 ng/mL r-basic FGF (recombinant basic fibroblast growth factor). $1.5 \times 10^5$ melanocytes and $5.0 \times 10^5$ keratinocytes were suspended in 80 μL MXSM, seeded onto the dermis, and incubated at 37° C. for 8 days at the air-liquid interface.

Example 2: Estrogen and Progesterone Reciprocally Regulate Melanin Synthesis

Figure 1:
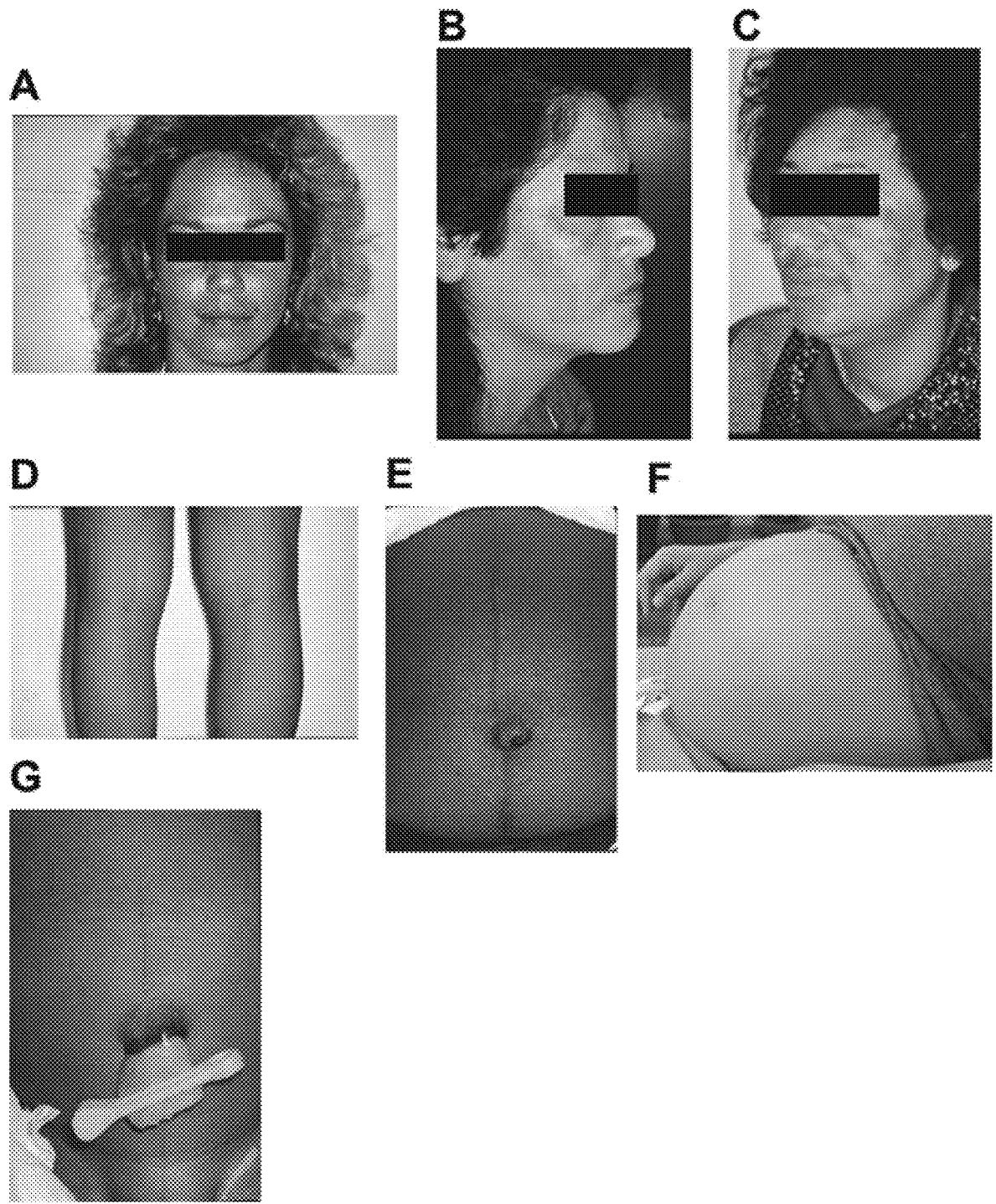
FIG. 1 comprises a set of images illustrating pregnancy-associated pigmentation disorder. Images A-C depict pigmentation disorder of patients with melasma. Image D depicts a patient with pigmentary demarcation lines. Images E and F depict typical linea nigra on a mother. Image G depicts typical linea nigra on a child.
Figure 2A:
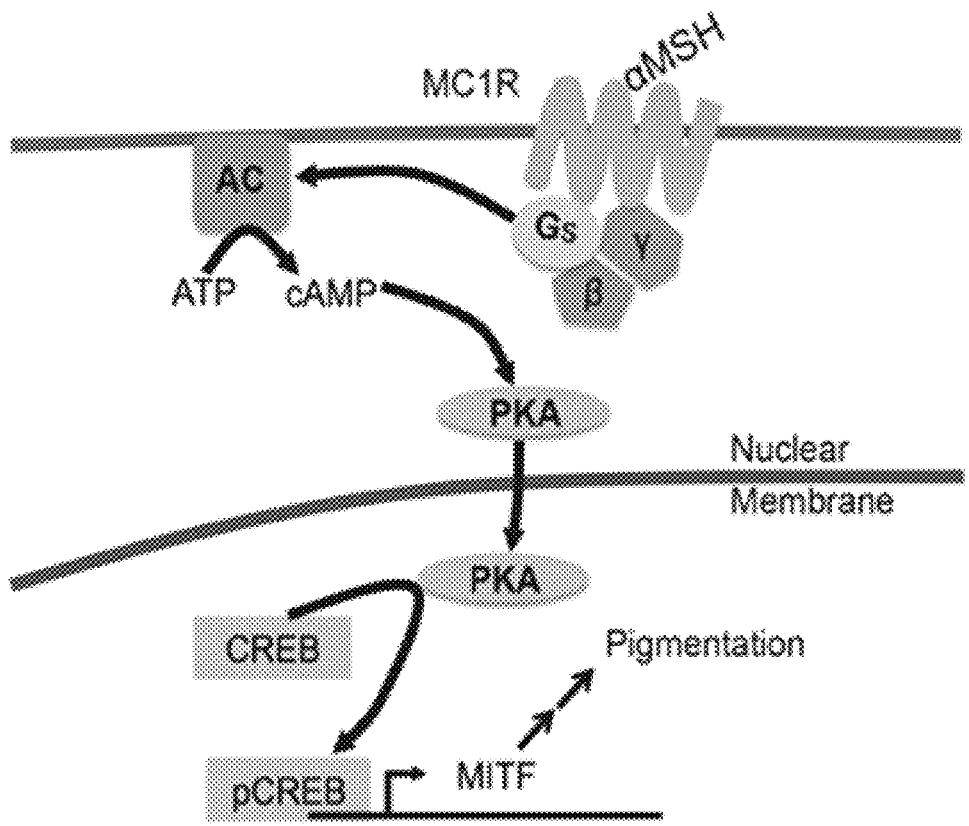
FIGS. 2A-2G comprise a set of scheme and bar graphs illustrating melanin production in human melanocytes.
Figure 2B:
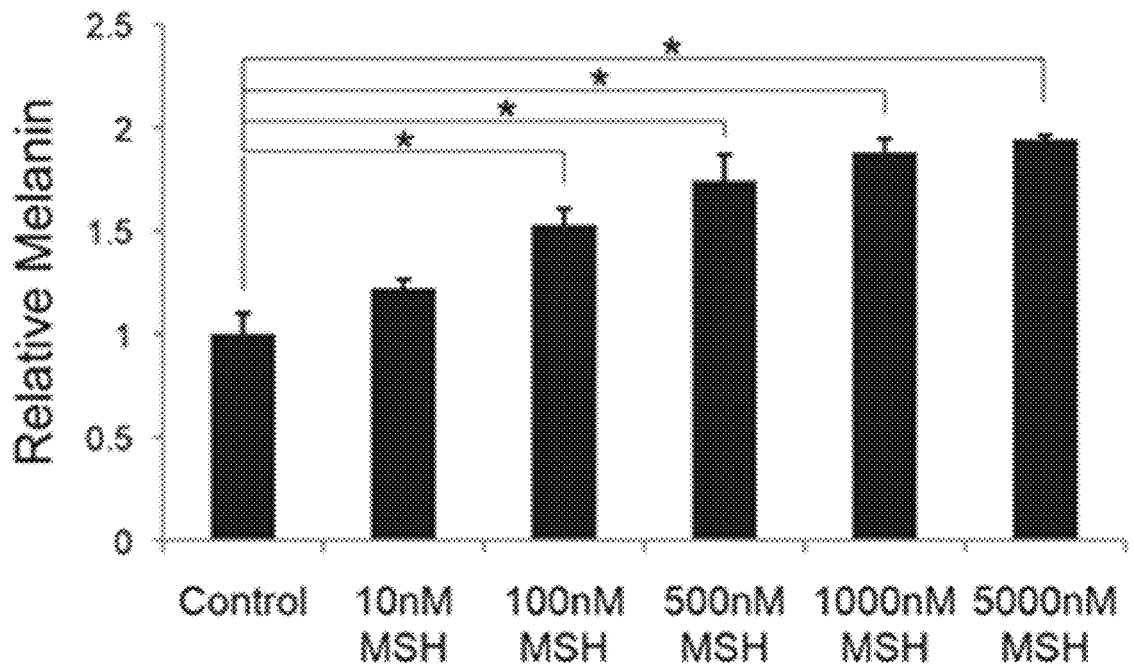
Figure 2C:
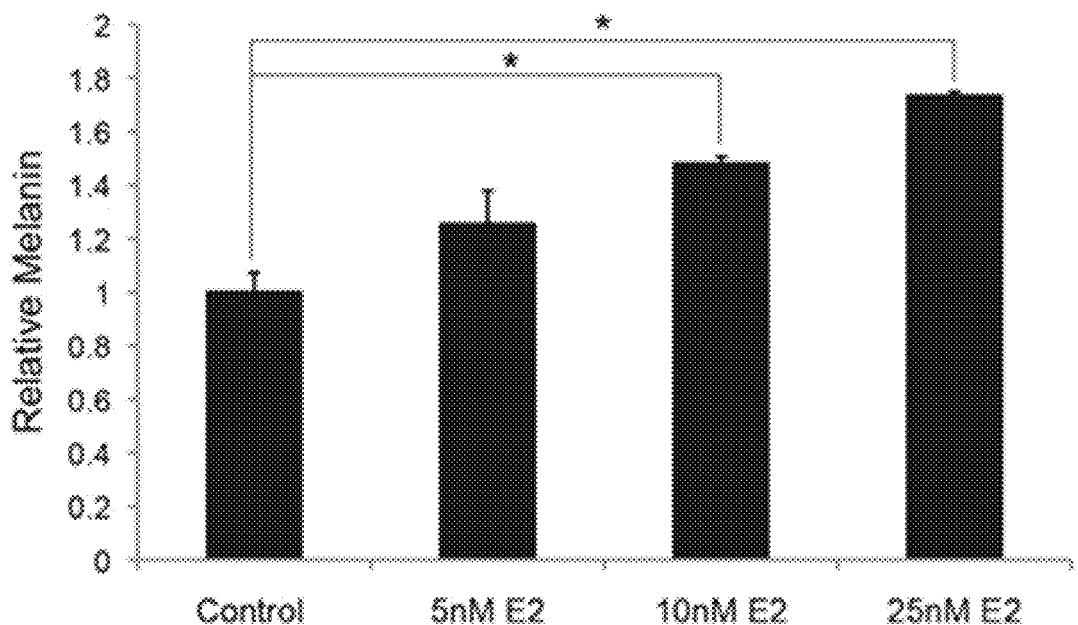
Figure 2D:
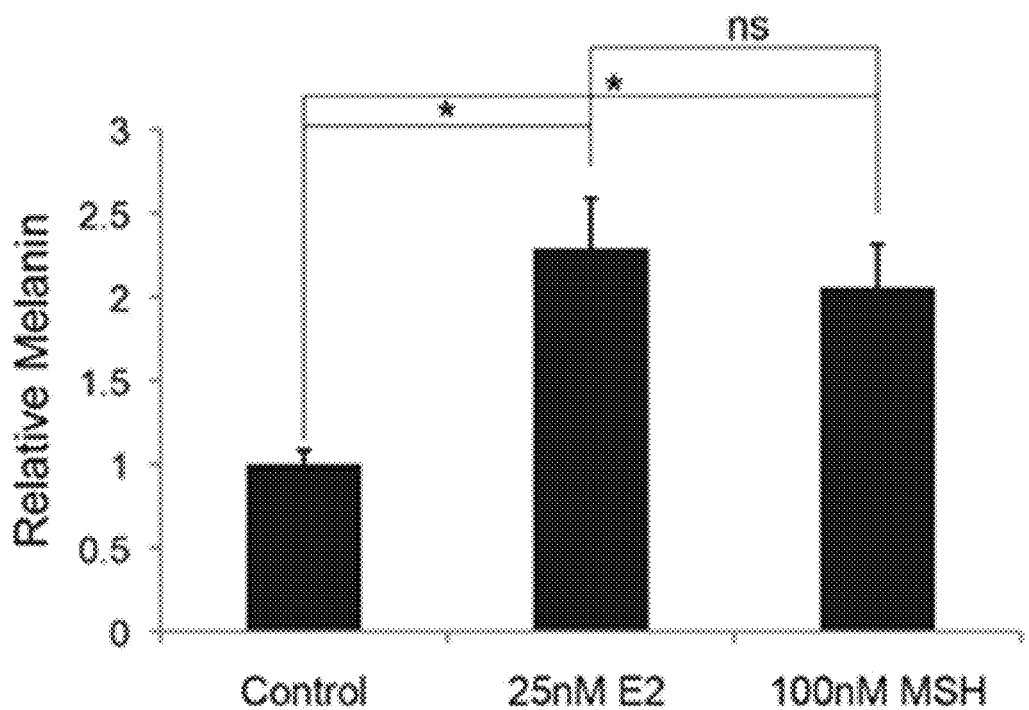

To examine whether sex steroids directly influence melanin synthesis, normal primary human melanocytes was treated with estrogen (17β-estradiol), which resulted in a dose dependent increase in melanin production (FIG. 2C). 25 nM estrogen were used for subsequent experiments, a medically-relevant concentration observed during second and third trimester pregnancy. After 4 days, melanin production was markedly increased (208±27%) (FIG. 3A). The change in melanin production was similar in magnitude to changes observed with αMSH (FIGS. 2B & 2D). This melanin-promoting estrogen effect was consistent with involvement of estrogen in melanin synthesis. To examine the effects of estrogen on melanocyte homeostasis in the context of intact human epidermis, architecturally-faithful 3-D organotypic skin was established utilizing normal primary epidermal keratinocytes and melanocytes within the framework of native stroma and intact basement membrane. After 1 week, estrogen-treated skin displayed a 3-fold increase in melanin content (FIG. 3B), without any increase in total melanocyte number or density (FIG. 3C).

Figure 2E:
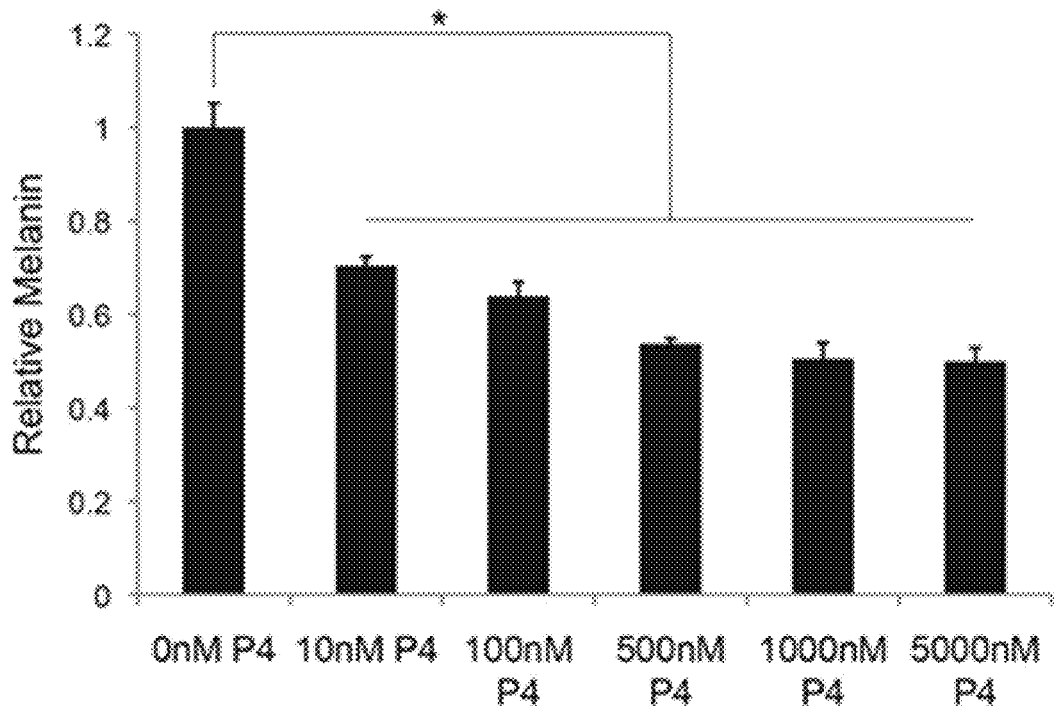

Physiologic estrogen effects in other tissue types are often counter-balanced by simultaneous exposure to progesterone, another sex steroid that increases markedly during pregnancy. To determine whether this reciprocal relationship is also active in melanocytes, cells were treated with physiologic levels of progesterone, which resulted in a dose dependent decrease in melanocyte melanin production (FIG. 2E). A concentration of 500 nM was used for subsequent experiments, a level reflective of that seen during $3^{rd}$ trimester pregnancy. Progesterone decreased melanin production by nearly half (58±11.4%), both in culture (FIG. 3D) and in skin tissue (FIG. 3E), without affecting overall melanocyte cell number (FIG. 3F).

Figure 2F:
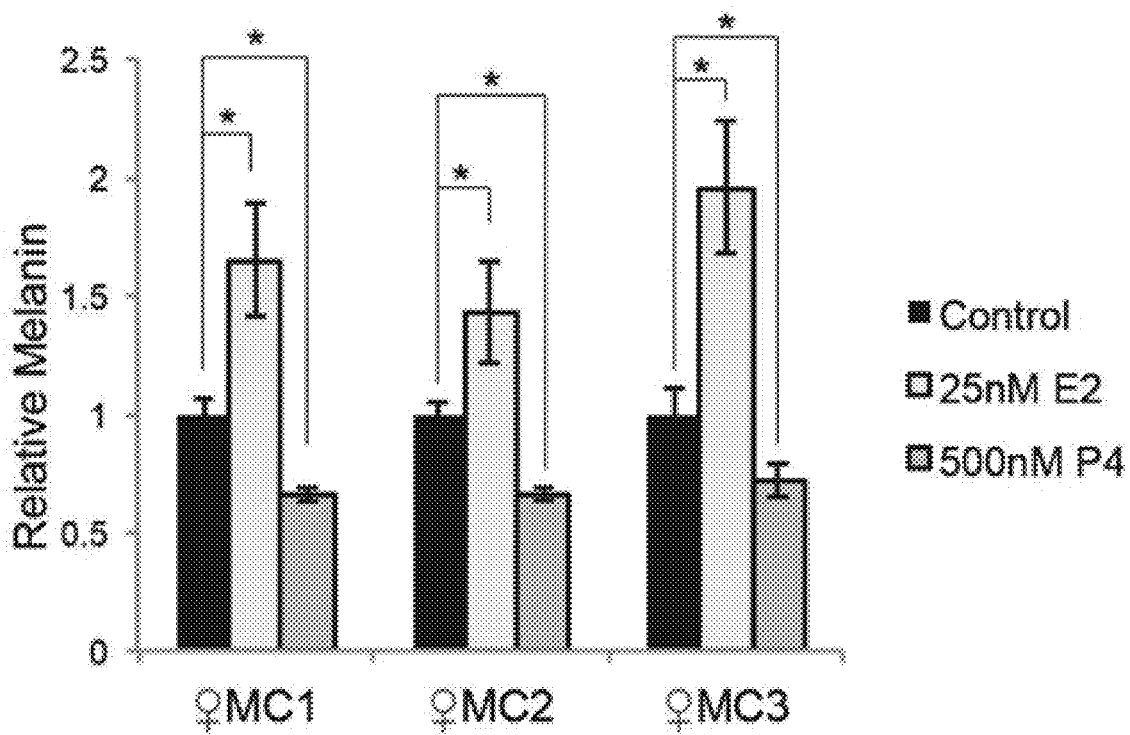

To determine whether female cells also responded similarly, female iPS-derived melanocytes were treated with estrogen and progesterone. Responses similar to those observed with the male cells were noted (FIG. 2F).

Figure 2G:
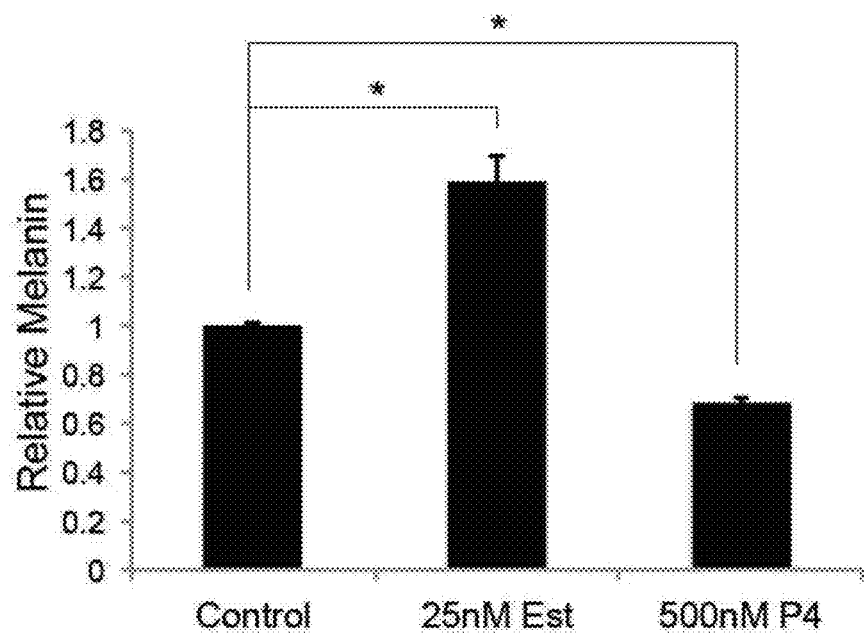

To determine whether melanocytes isolated from body sites other than foreskin also responded similarly to sex hormones, melanocytes from adult facial skin were treated with estrogen and progesterone; responses observed were similar to those observed with the foreskin melanocytes (FIG. 2G).

Figure 4A:
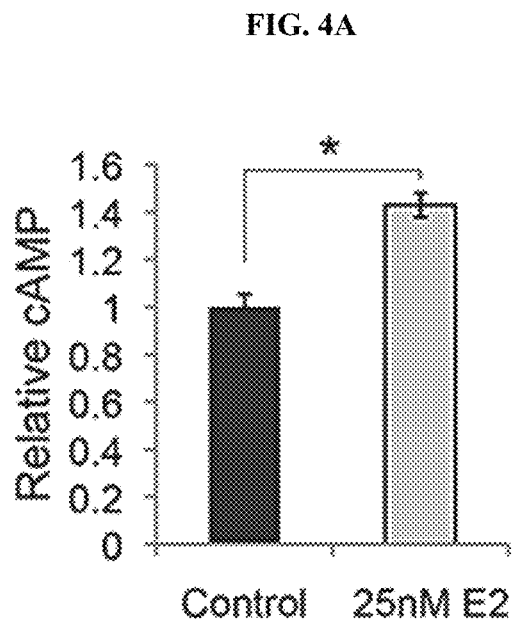
FIGS. 4A-4H comprise a set of images and bar graphs illustrating the finding that estrogen and progesterone access the classical melanin production pathway through nonclassical receptors.
Figure 4B:
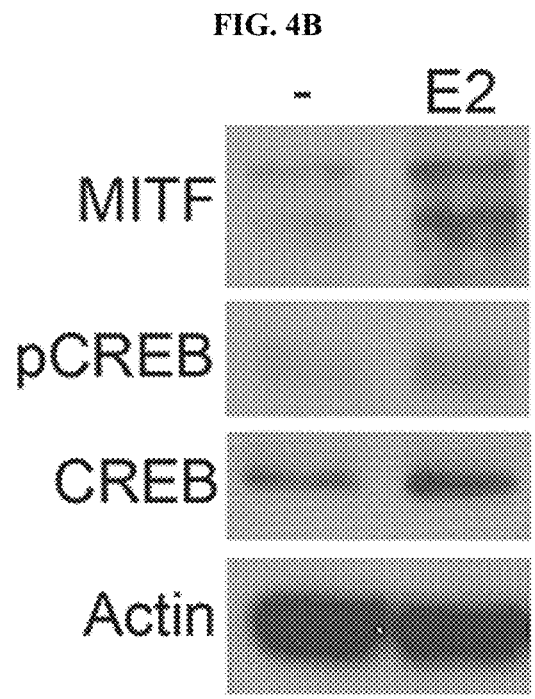
Figure 4C:
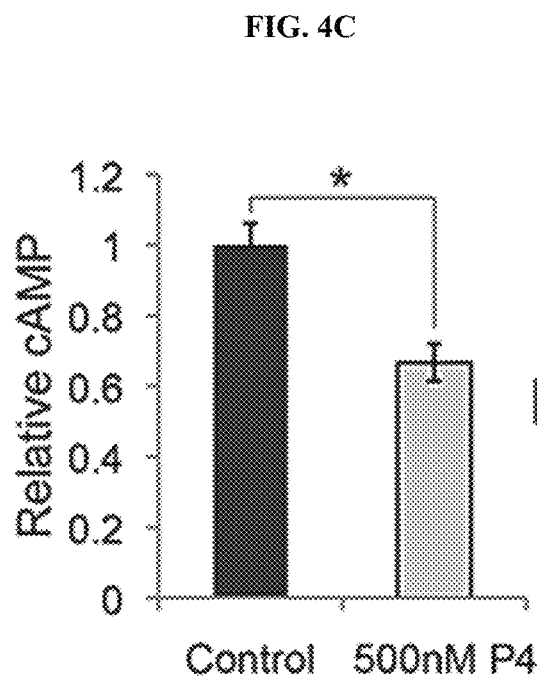
Figure 4D:
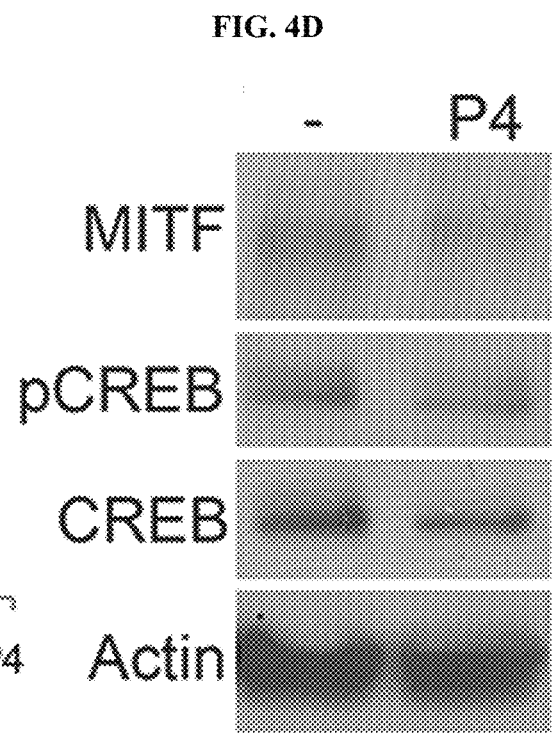

Example 3: Primary Human Melanocytes do not Express Nuclear Estrogen or Progesterone Receptors (ER/PR), and Respond to Sex Steroids Via Altered cAMP Signaling To determine the mechanisms through which estrogen and progesterone mediate their pigment effects, components of the canonical pigment production pathway were examined. An increase in cAMP upon estrogen treatment (FIG. 4A) was observed. This suggests that estrogen accesses the canonical pigment production pathway downstream of MC1R. Consistent with this, pCREB and MITF proteins were similarly induced (FIG. 4B). In contrast, progesterone treatment resulted in diminished pigment production, with corresponding decreases in cAMP, pCREB and MITF (FIGS. 4C-4D).

Figure 4E:
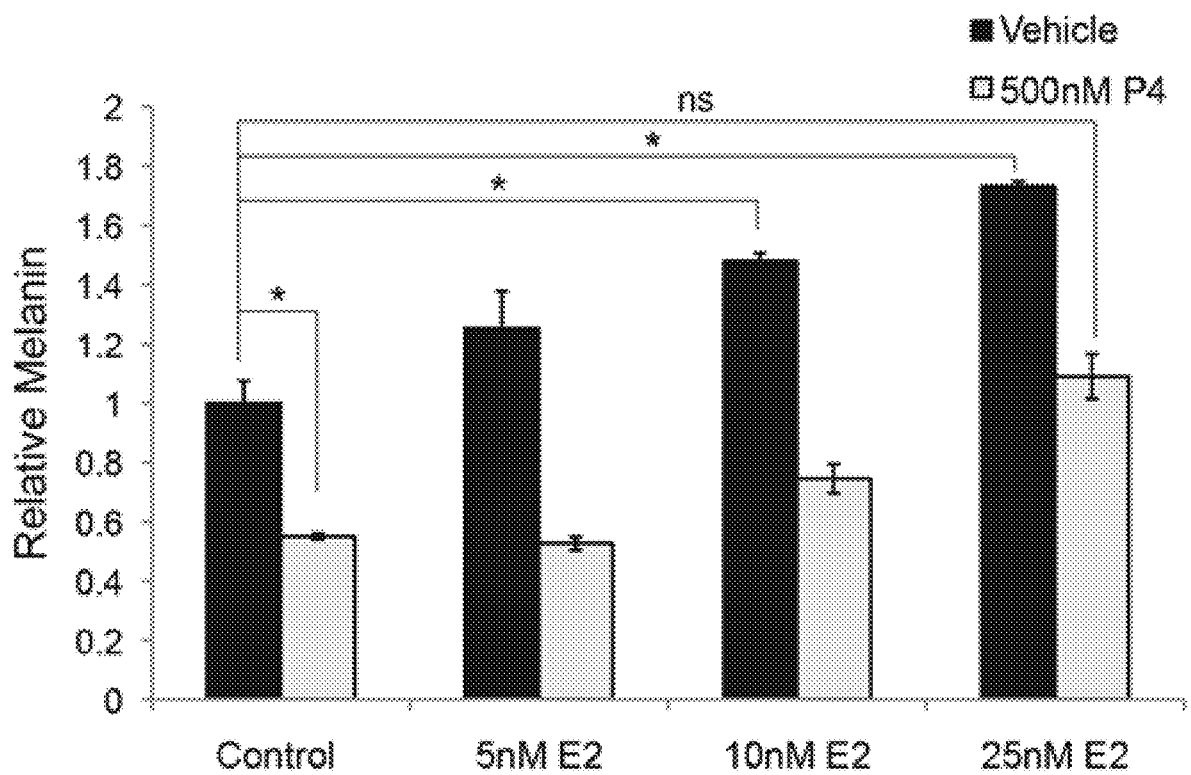

Without wishing to be limited by any theory, these data suggest that estrogen, progesterone, and α-MSH converge on the canonical melanin production pathway at the level of adenylate cyclase to reciprocally modulate melanin synthesis. Consistently, the estrogen pigment effects were significantly attenuated in the presence of physiologic progesterone (FIG. 4E). This likely explains why pregnancy-associated hyperpigmentation is not observed all over the body, but is characteristically limited to specific areas where melanocyte density or UV radiation exposure is highest, including the face, genital, and areolar regions.

Figure 4F:
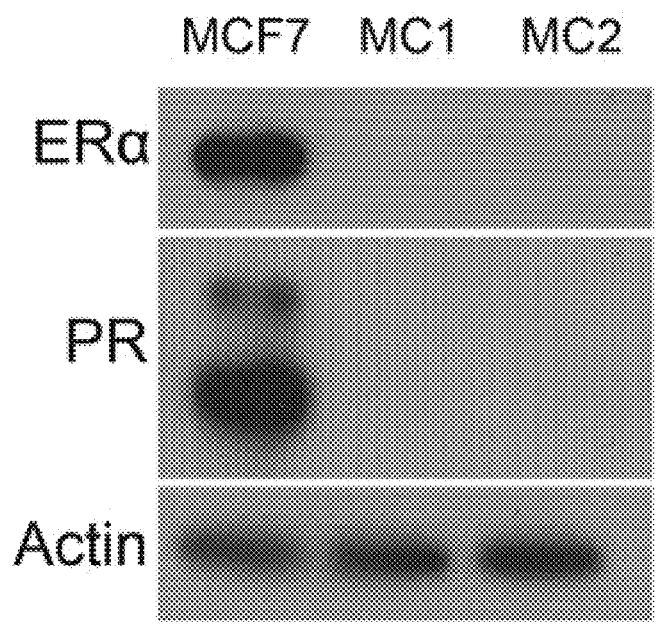

As steroid hormones are not predicted to signal through MC1R, which natural ligand is the peptide hormone αMSH, efforts were put forth to identify the specific receptors through which estrogen and progesterone mediate their effects on melanin synthesis. Classical estrogen (ER) and progesterone (PR) receptors were not detected in melanocytes using qRT-PCR, despite robust expression in the MCF7 ER/PR positive breast cell line (FIG. 5A). RNAseq studies in primary human melanocytes failed to detect ER or PR transcripts (FIG. 5B). No ER or PR protein was detected via western blotting of melanocyte protein lysates, although both receptors were readily apparent in MCF7 extracts (FIG. 4F).

Figure 4G:
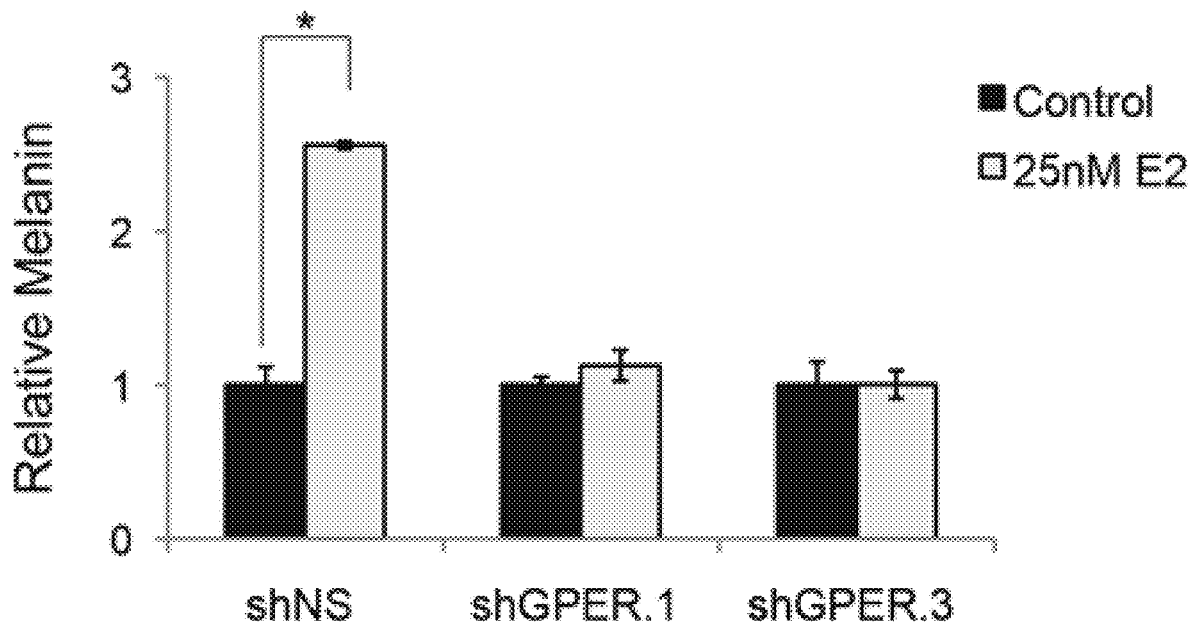
Figure 4H:
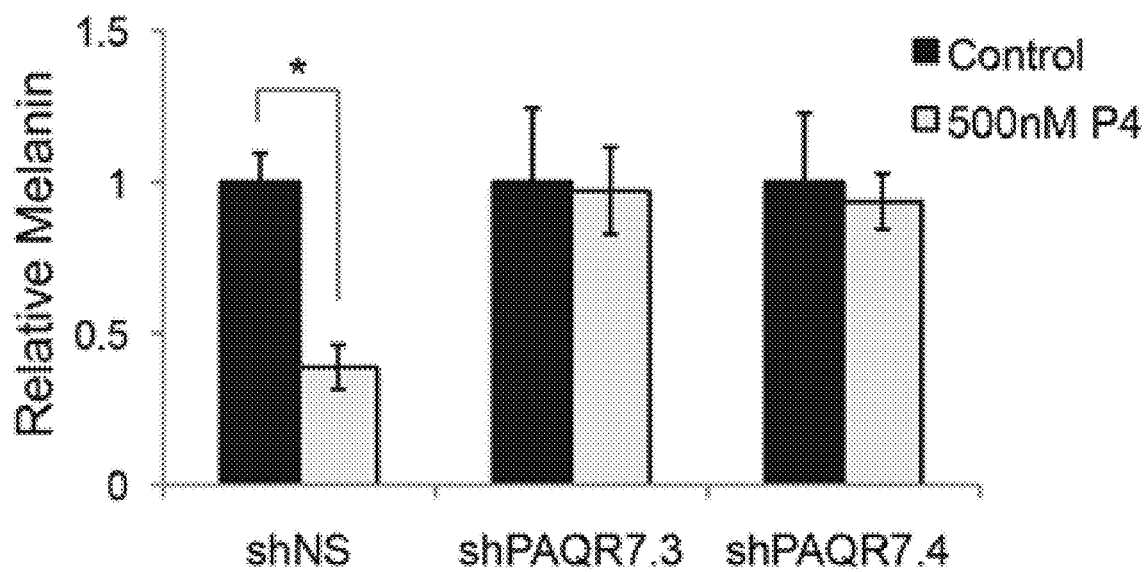
Figure 5E:
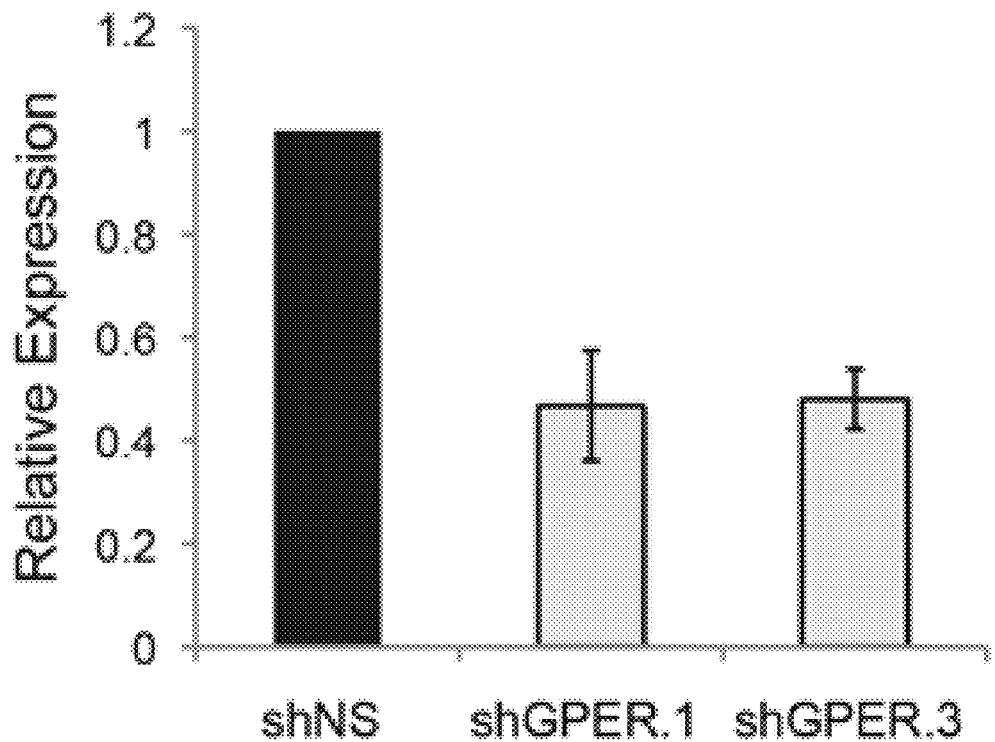
Figure 5F:
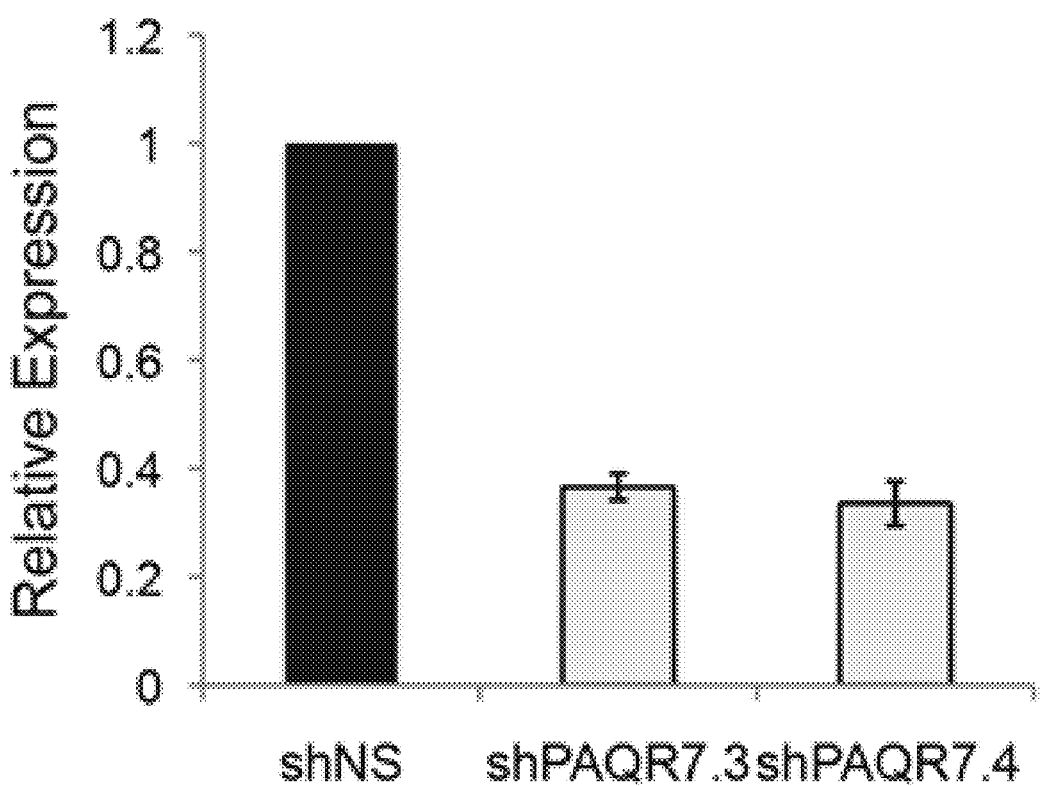

Example 4: Sex Steroid Signaling in Melanocytes is Dependent on the Nonclassical Membrane Bound G-Protein Coupled Sex Hormone Receptor GPER Since MC1R is a G protein-coupled receptor (GPCR), it was hypothesized that an alternative GPCR may be binding sex hormones to mediate pigment effects. To identify possible candidates, whole transcriptome RNAseq data from primary human MCs to identify other expressed GPCRs were analyzed. The membrane-bound, G protein-coupled estrogen receptor (GPER) was expressed (FIG. 5B). An analoguous, noncanonical G protein-coupled progesterone receptor, porogestin and adipoQ receptor 7, was also detected (FIG. 5B). Primary human MCs were analyzed for expression of GPER and PAQR7 by qRT-PCR, and their expressions were verified (FIG. 5C). Notably, GPER and PAQR7 expressions were markedly lower in other skin cell types including keratinocytes and fibroblasts (FIG. 5D).

shRNA-mediated knockdown was utilized to establish the necessity of GPER and PAQR7 to mediate sex hormone effects in MCs (FIGS. 5E-5F). GPER or PAQR7 depletion using either of two independent hairpins completely eliminated the melanocyte pigmentation response to estrogen and progesterone, respectively (FIGS. 4G-4H).

Figure 5G:
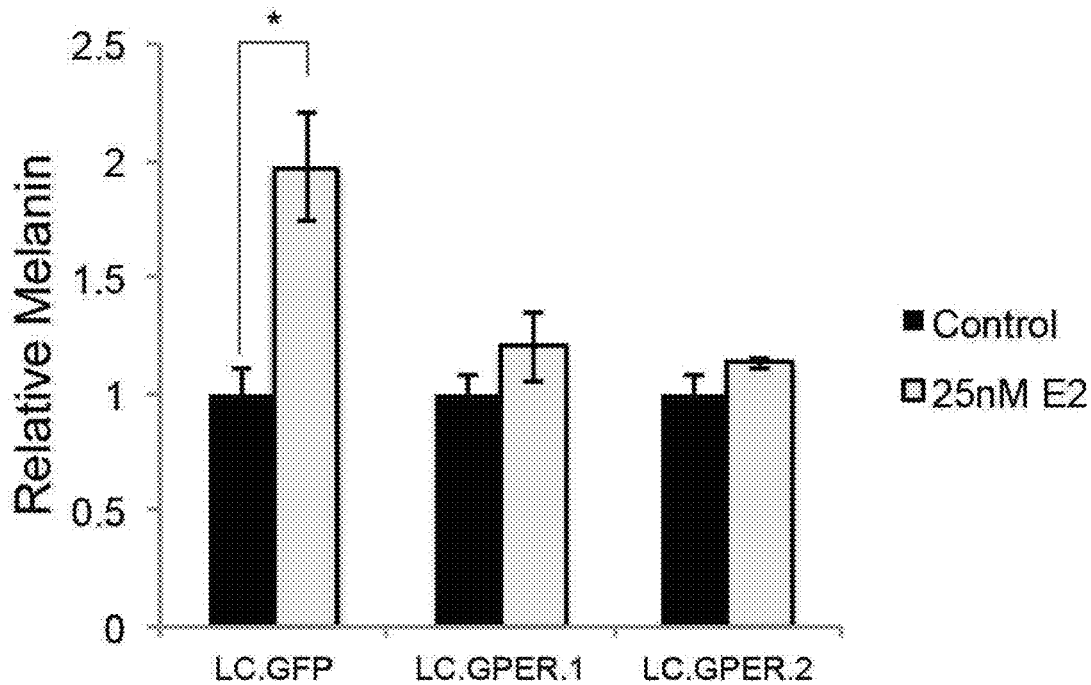
Figure 5H:
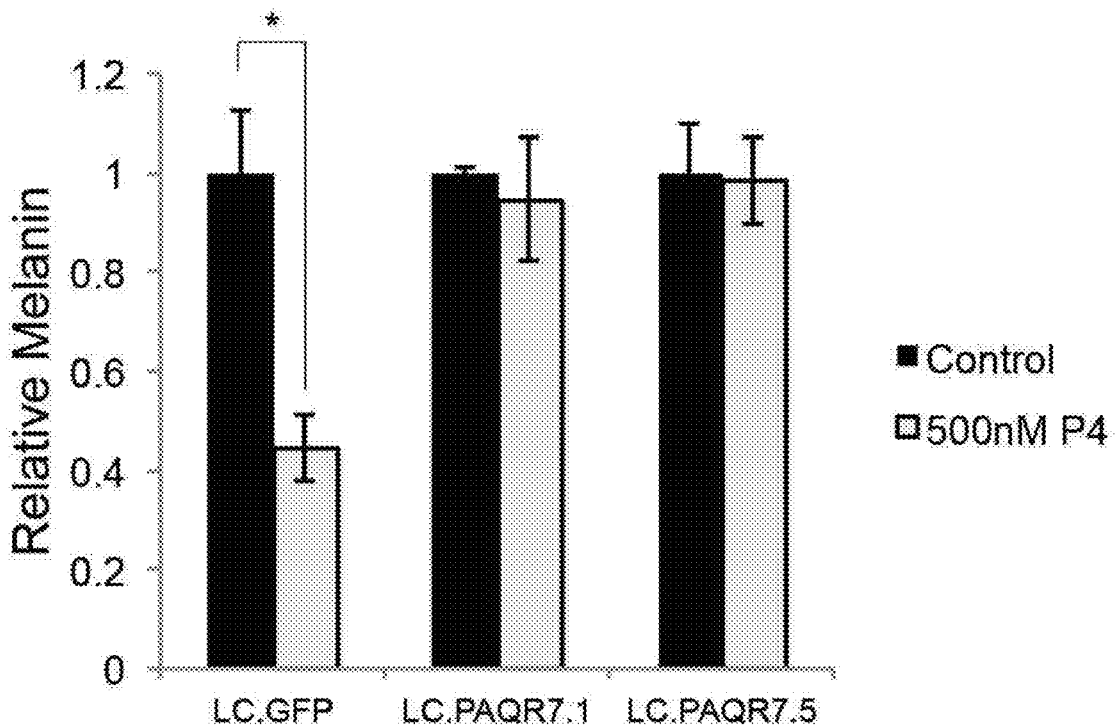

To verify these results, a complementary genetic approach based on CRISPR-Cas9 mediated gene disruption of GPER or PAQR7 was used, which also completely blocked the pigmentary response to estrogen and progesterone, respectively (FIGS. 5G-5H).

Figure 6:
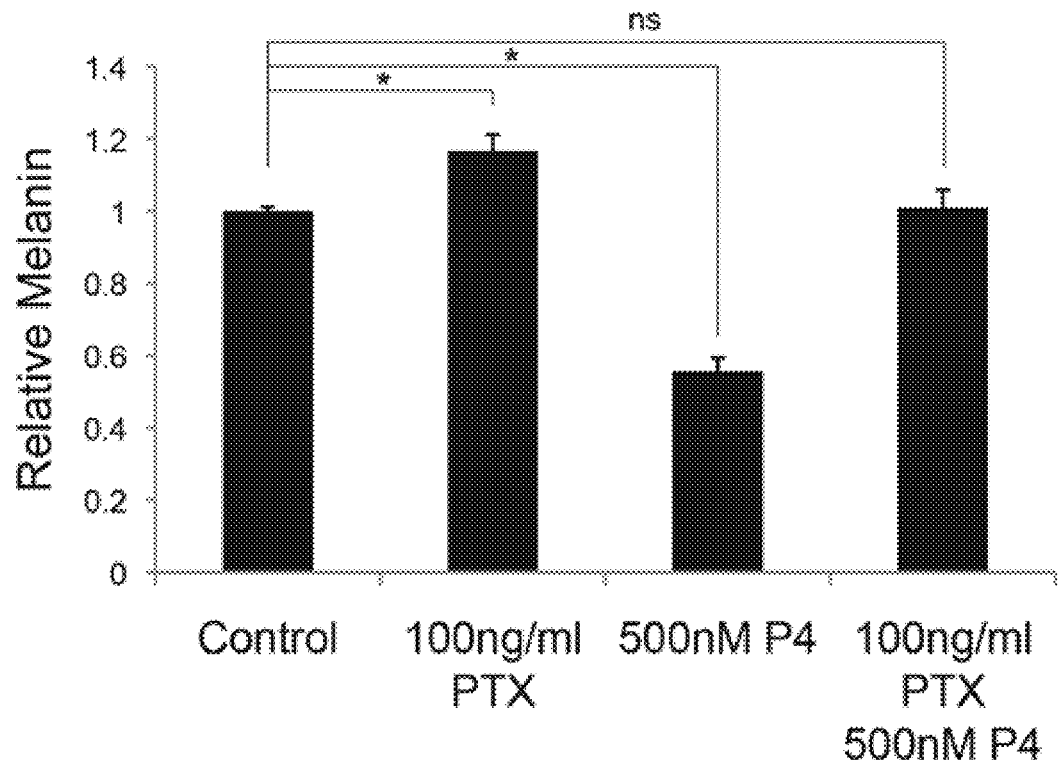
FIG. 6 is a bar graph illustrating melanin synthesis in response to Pertussis Toxin (PTX), progesterone (P4), or both. N=3 biologic replicates for each experiment. Error bars denote ±s.d., *p<0.05.

PAQR7 binds progesterone and regulates the final stages of sea trout oocyte meiosis through cAMP reduction. In that fish system, PAQR7 signals through G protein complexes containing the inhibitory G subunit (G). G subunits function to repress adenylate cyclase, resulting in a decrease in cytosolic cAMP. To examine whether this signaling mechanism was also functional and relevant in mammals, primary human melanocytes were treated with progesterone in the presence of pertussis toxin (PTX), an exotoxin that catalyzes the ADP-ribosylation of G subunits. This modification prevents G from interacting with GPCRs, and therefore prevents their activation upon GPCR ligand binding. Treatment of melanocytes with PTX completely blocked progesterone pigment effects, establishing that progesterone signals through G subunits in melanocytes (FIG. 6). The finding that PAQR7 works through inhibitory G subunits is interesting, as it the first example of a melanocyte cellular signaling cascade that actively represses melanin synthesis at the level of G-protein signaling, as opposed to classically defined pigment control mechanisms that modulate the strength of the stimulatory MC1R signal. In many animal systems, the Agouti protein decreases pigment production via physically binding to MC1R and inhibiting αMSH stimulation, rather than through an actively suppressive mechanism.

Figure 7A:
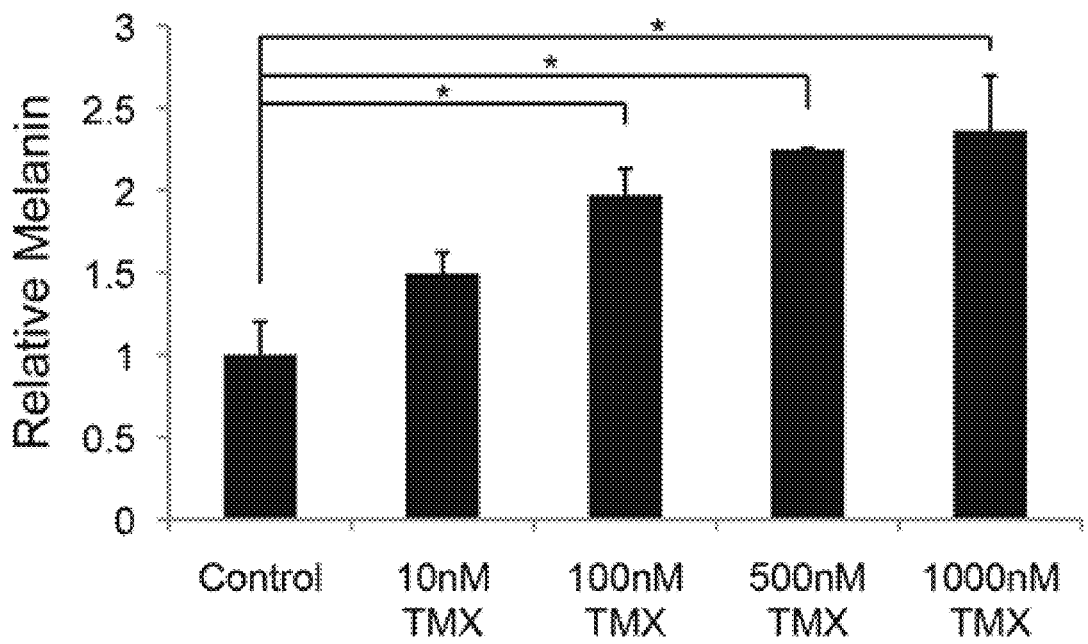
FIGS. 7A-7B comprise a set of bar graphs illustrating the finding that melanin production is altered by sex steroid analogs—GPER agonists currently in clinical use.
Figure 7B:
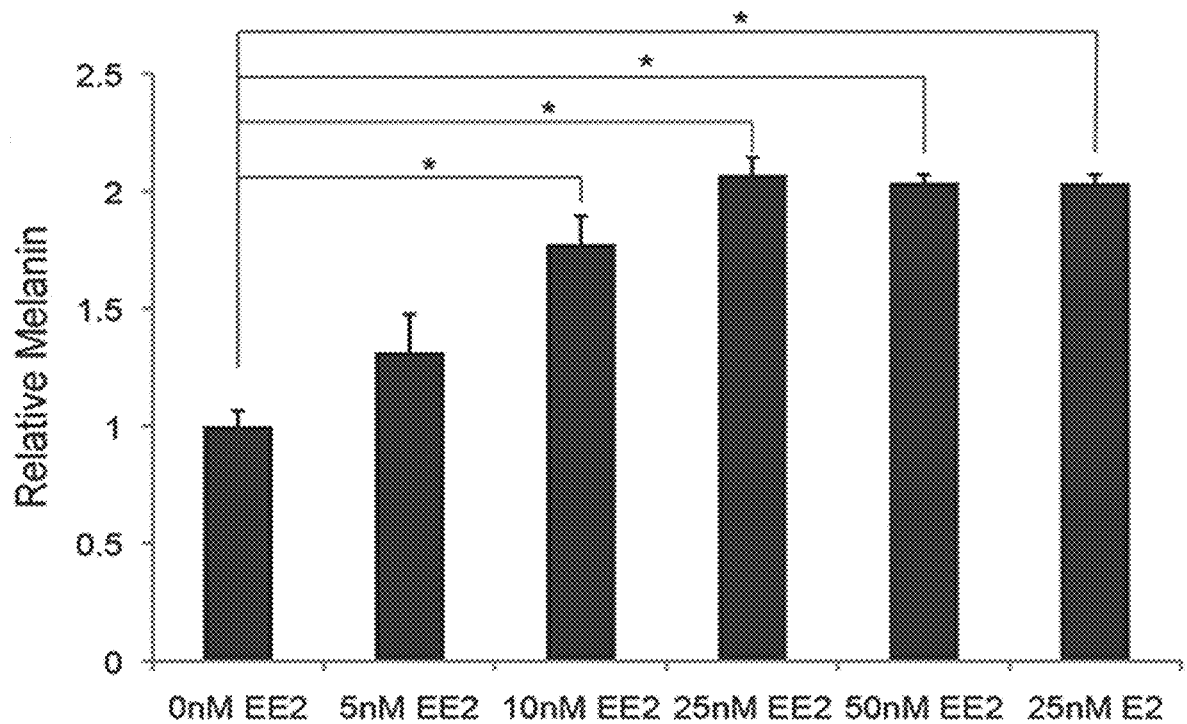

Example 5: Specific Activation of GPER Alters Pigment Production in Human Skin Tissue To complement these genetic studies establishing that estrogen and progesterone pigment effects are mediated through nonclassical sex steroid receptors, small molecule steroid analogs were utilized with specific agonist activity on ER, PR, GPER or PQAR7. Tamoxifen, an ER antagonist, is associated with development of melasma in breast cancer patients. The mechanistic basis for this clinical observation was previously unknown and somewhat perplexing, given that tamoxifen blocks estrogen receptor function and thus might have been predicted to limit melanin synthesis. However, tamoxifen acts as a GPER agonist. Tamoxifen treatment resulted in a dose-dependent increase in melanin production to levels comparable to those observed with native estrogen (FIG. 7A), consistent with the model in which GPER activation promotes melanin synthesis. Most oral contraceptives incorporate an estrogen derivative (ethinyl estradiol) for the estrogen component. Treatment of primary human MCs with ethinyl estradiol also resulted in a dose dependent increase in melanin production, indistinguishable from native estrogen at an equal concentration (FIG. 7B).

Figure 8:
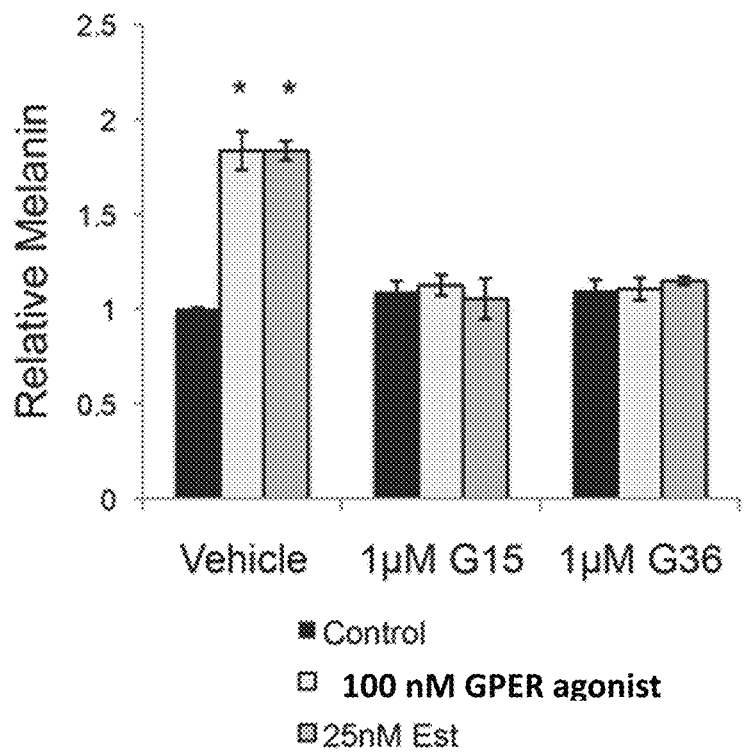
FIG. 8 comprises a bar graph illustrating melanin production by melanocytes treated with vehicle, a GPER agonist, or estrogen, in the presence of selective GPER antagonists G-15 or G-36. N=3 biologic replicates for each experiment. Error bars denote ±s.d., *p<0.05.
Figure 9A:
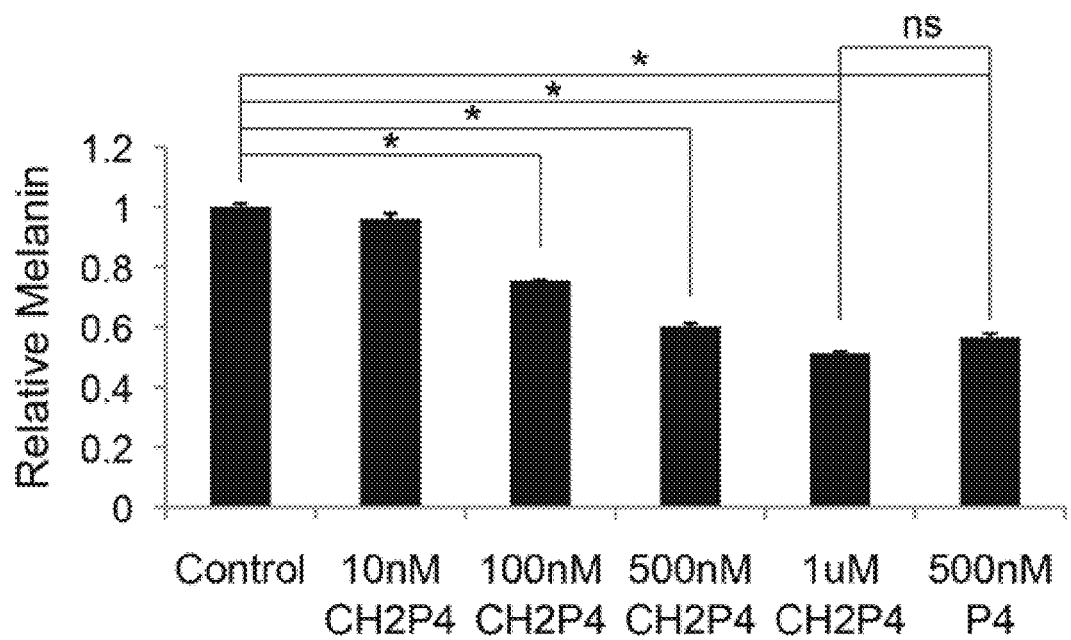
FIGS. 9A-9B comprise a set of bar graphs illustrating the effects of specific agonists targeting PAQR7 on melanin production.
Figure 9B:
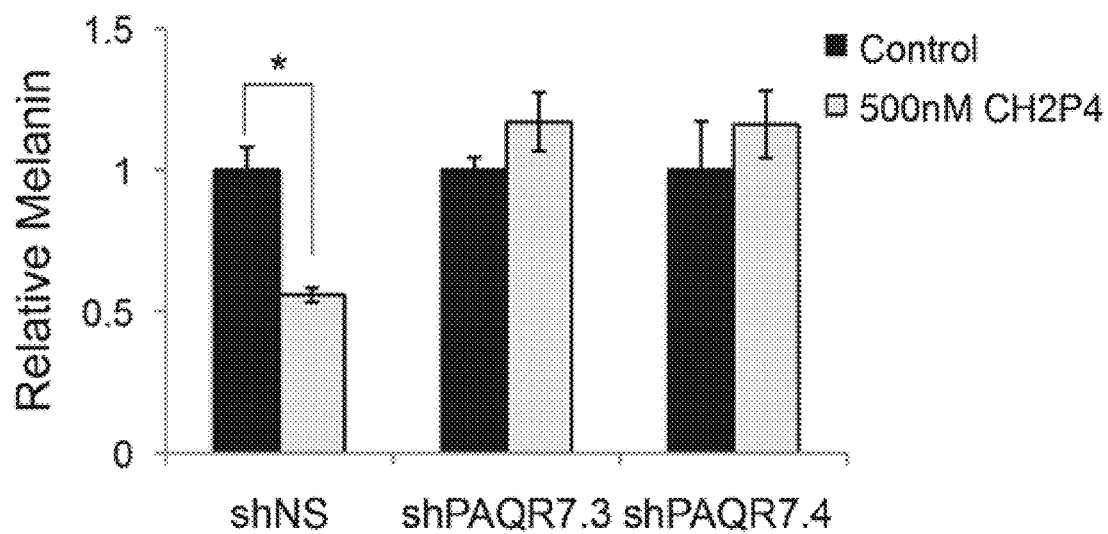
Figure 10A:
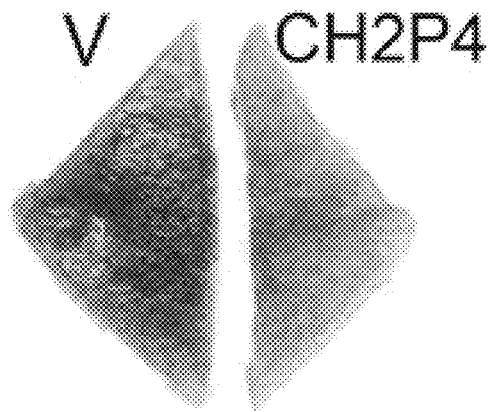
FIGS. 10A-10C comprise a set of images and bar graphs illustrating the finding that GPER signaling is sufficient to alter melanin production in organotypic human tissue.
Figure 10B:
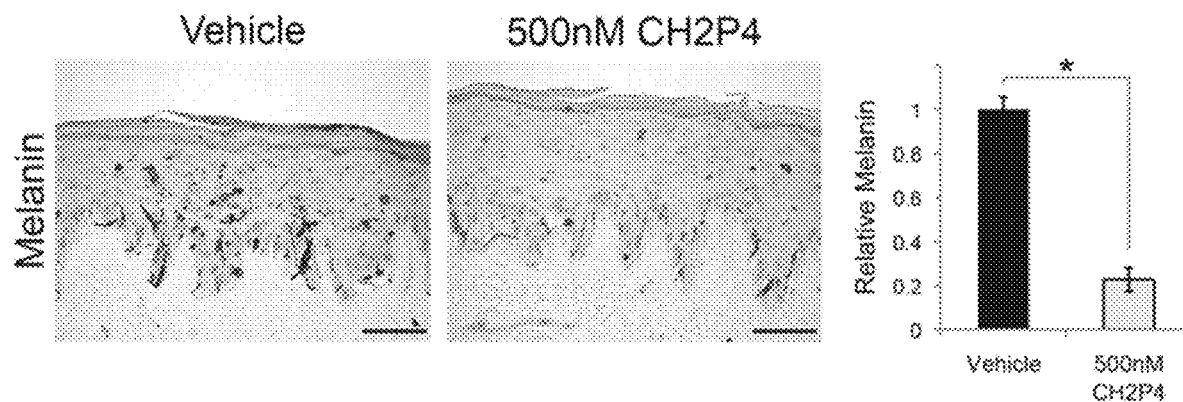
Figure 10C:
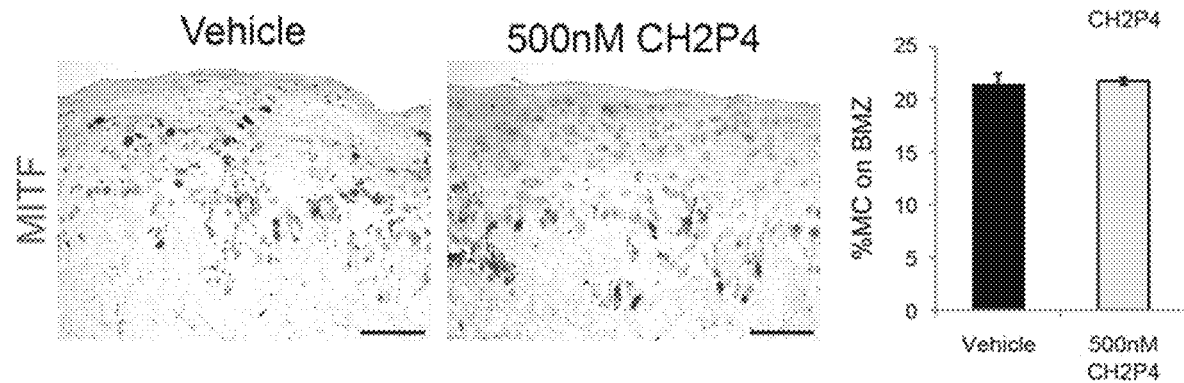

Further establishing that GPER is the melanocyte estrogen receptor, a GPER agonist (G-1; rel-1-[4-(6-bromo-1,3-benzodioxol-5-yl)-3aR,4S,5,9bS-tetrahydro-3H-cyclopenta [c]quinolin-8-yl]-ethanone) and estrogen effects were blocked by either of two specific GPER antagonists, G-15 and G-36 (FIG. 8), which do not have inhibitory activity against ER. To establish that PAQR7 signaling is sufficient to decrease melanin production, a specific PAQR7 agonist Org OD-02 ($CH_2P4$), which does not bind PR, was used. $CH_2P4$ caused a dose-dependent, PAQR7-dependent, decrease in melanin production (FIGS. 9A-9B and 10A-10C).

Example 8: In Vivo Studies

Tissue generated elsewhere herein is orthotopically xenografted onto immunocompromised mice, allowing analysis of human skin in vivo. Hormones are administered subcutaneously or topically to demonstrate the necessity of GPER to mediate hormone-induced changes in pigmentation. The effects of the specific agonists are evaluated.

To demonstrate that this mechanism is not restricted to foreskin-derived melanocytes, melanocytes are isolated from various body sites and donors of different age, sex, and race. 3-D organotypic cultures are established with melanocytes from these sources, and the necessity and sufficiency of GPER signaling is evaluated.

Example 9: Evaluation of Mechanism Through which GPER Influences Pigmentation

To analyze the mechanism through which estrogen and progesterone influence pigmentation downstream of GPER, the Ga subunit activated by the receptor is identified. To accomplish this, agonist-promoted [$^{35}$S]GTPγS exchange assays are used, followed by immuno-enrichment of specific G protein subgroups. G protein-coupled receptor signaling drives guanine nucleotide exchange on the Ga subunit, switching GDP for GTP. [$^{35}$S]GTPγS is an isotopic, non-hydrolysable analogue of GTP. Membrane preparations from primary human melanocytes are isolated and stimulated with GPER agonist, as well as vehicle controls, in the presence of [$^{35}$S]GTPγS. Next, Gs and Gi subunits are immunoprecipitated from the samples, and [$^{35}$S]GTPγS binding is measured using a scintillation spectrophotometer. Melanocytes with ablated GPER are used as negative controls in these assays.

Both the Gs and Gi subunits influence adenylate cyclase activity, which functions to produce cAMP. To examine the mechanism through which GPER is regulating the canonical pigmentation pathway downstream of G protein signaling, adenylate cyclase activity is analyzed in the presence of estrogen and progesterone using cAMP ELISA, relative to vehicle-treated controls. Western analysis is used to examine downstream changes in pCREB and MITF relative to vehicle-treated controls.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of decreasing or reversing gain of skin pigmentation in a mammalian subject, the method comprising:

selecting a mammalian subject with pigmentary changes to the skin associated with a condition selected from the group consisting of oral contraceptive use, pregnancy, endogenous estrogens in females, solar lentigo, eczema, chemical burn scars, sun burn scars, thermal burn scars, lupus, psoriasis, sarcoidosis, pityriasis, erythema dyschromicum perstans, blistering diseases, drug reactions, and lichen planus;

topically or transdermally administering to the mammalian subject a pharmaceutical composition comprising at least one pharmaceutically acceptable excipient and a therapeutically effective amount of a PAQR7 (Progestin and AdipoQ Receptor 7) agonist, wherein the PAQR7 agonist is:

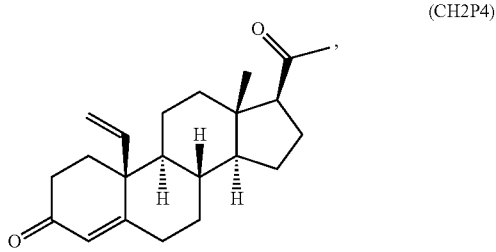

(CH2P4)

or a salt, solvate, tautomer, enantiomer, or diastereomer thereof; and reducing the amount of melanin in the skin of the mammalian subject in a dose-dependent manner, wherein the PAQR7 agonist decreases or reverses gain of skin pigmentation in the mammalian subject, and wherein the CH2P4 does not bind to a canonical progesterone receptor (PR) in the mammalian subject.

2. The method of claim 1, wherein the pharmaceutical composition further comprises at least one selected from the group consisting of a sun-blocking agent and a sunscreen lotion.

3. The method of claim 1, wherein the pharmaceutical composition is essentially free of a skin bleaching agent.

4. The method of claim 1, wherein the mammalian subject is human.

5. The method of claim 1, wherein the pharmaceutical composition comprises about 0.005% to about 10% (w/w) of CH2P4.

6. The method of claim 1, wherein the pharmaceutical composition comprises about 0.005% to about 1% (w/w) of CH2P4.

7. The method of claim 1, wherein the pharmaceutical composition comprises at least one of a permeation enhancer and a hydrotropic agent.

8. The method of claim 1, wherein the condition is selected from the group consisting of oral contraceptive use, pregnancy, endogenous estrogens in females, solar lentigo, eczema, lupus, psoriasis, sarcoidosis, pityriasis, erythema dyschromicum perstans, blistering diseases, drug reactions, and lichen planus.

* * * * *